(12) United States Patent
Breipohl et al.

(10) Patent No.: US 6,465,650 B1
(45) Date of Patent: Oct. 15, 2002

(54) SUBSTITUTED N-ETHYLGLYCINE DERIVATIVES FOR PREPARING PNA AND PNA/DNA HYBRIDS

(75) Inventors: Gerhard Breipohl, Frankfurt; Eugen Uhlmann, Glashütten; Jochen Knolle, Kriftel, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/506,901

(22) Filed: Feb. 18, 2000

Related U.S. Application Data

(62) Division of application No. 08/402,840, filed on Mar. 13, 1995, now Pat. No. 6,075,143.

(51) Int. Cl.[7] ............... C07D 473/16; C07D 473/18; C07D 473/34; C07D 239/54; C07D 473/00
(52) U.S. Cl. ............... 544/264; 544/265; 544/266; 544/271; 544/276; 544/277; 544/280; 544/311; 544/312; 544/316; 544/317; 548/255; 548/264.4; 548/265.4; 548/267.7; 548/324.1; 548/326.5; 548/327; 548/327.5; 548/328.5; 548/333.1; 548/332.5; 548/338.1
(58) Field of Search ............... 544/264, 265, 544/266, 271, 276, 277, 280, 311, 312, 316, 317; 548/255, 264.4, 265.4, 267.7, 324.1, 326.5, 327, 327.5, 328.5, 333.1, 332.5, 338.1

(56) References Cited

U.S. PATENT DOCUMENTS

| | | | | |
|---|---|---|---|---|
| 4,167,508 | A | 9/1979 | Wunsch | 424/177 |
| 4,213,893 | A | 7/1980 | Carrico | 536/26 |
| 4,213,968 | A | 7/1980 | Kastina | 424/177 |
| 4,284,721 | A | 8/1981 | Oyama | 435/70 |
| 4,808,716 | A | 2/1989 | Hol | 544/244 |
| 5,144,035 | A | 9/1992 | Mase | 544/295 |
| 5,227,497 | A | 7/1993 | Inoue | 544/353 |
| 5,470,974 | A | 11/1995 | Summerton | 544/118 |
| 5,480,899 | A | 1/1996 | Yano | 514/376 |
| 5,614,498 | A | 3/1997 | Ishikawa | 514/18 |
| 5,623,049 | A | 4/1997 | Lobberding | 530/300 |
| 5,646,143 | A | 7/1997 | Goschke | 544/148 |
| 6,172,226 | B1 * | 1/2001 | Coull et al. | 544/317 |
| 6,265,559 | B1 * | 7/2001 | Glidea et al. | 544/277 |

FOREIGN PATENT DOCUMENTS

| | | |
|---|---|---|
| EP | 0 460 446 | 12/1991 |
| GB | 93307455 | 9/1993 |
| WO | WO 92/20702 | 11/1992 |
| WO | WO 93/12129 | 6/1993 |
| WO | WO 94/25477 | 11/1994 |
| WO | WO 95/17403 | 6/1995 |

OTHER PUBLICATIONS

Stretwieser et al, "Introduction to Organic Chemistry, 4th Edition" Prentice Hall, pp 846–847, 1992.*
"Solid Phase Peptide Synthesis", Stewart et al, 1969, unnumbered page.*
Webb, JACS, (1986) 108:2764.
Barton, "Protective Groups in Organic Chemistry" (Plenum Pub, New York, NY) (1983) p. 43–66.
Hubbuch, "Schutzgrouppen in der Peptidsynthese" Kontact 3/79 (1990) pp. 16–18.

(List continued on next page.)

*Primary Examiner*—Mark L. Berch
(74) *Attorney, Agent, or Firm*—Finnegan, Henderson, Farabow, Garrett, & Dunner L.L.P.

(57) ABSTRACT

The invention provides a processes for the preparation of a compound of Formula I, or a salt thereof (I)

$$PG-X-\underset{\underset{Y}{|}}{\overset{B'}{\underset{|}{}}}\text{...}$$

wherein PG is a urethane- or trityl-type protective group; X is NH, O, or S; Y is $CH_2$, O, or NH; and B' is a base customary in nucleotide chemistry. The processes include reacting a compound of Formula (II)

(II)

with a compound of Formula (III)

(III)

a compound of Formula (V)

$$B'-CH_2-CO-R^2 \qquad (V),$$

a monohaloacetic acid derivative in a suitable solvent with an auxiliary base, or a compound of Formula (VII)

$$B'-CH_2-CO-R^3 \qquad (VII),$$

and converting the resulting compounds to that of Formula I.

7 Claims, No Drawings

OTHER PUBLICATIONS

Barlos, Peptides, (Escome Sci. Publishers BV) (1993) pp. 283–284.

Farese, Tet. Letters 37 (1996) 1413.

Thompson, Tetrahedron, 51 (1995) 6179.

Michael Egholm et al., "Peptide Nucleic Acids Containing Adenine or Guanine Recognize Thymine and Cytosine in Complementary DNA Sequences," Journal of the Chemical Society, Chemical Comm. (1993) pp. 800–801.

Chris Meier et al., "Peptide Nucleic Acids (PNAs)—Unusual Properties of Nonionic Oligonucleotide Analogues," Angewandte Chemie, vol. 31, No. 8, Aug. 1992, pp. 1008–1010.

Michael Egholm et al., "Peptide Nucleic Acids (PNA) Oligonucleotide Analogues with an Achrial Peptide Backbone," Journal of the American Chemical Society, vol. 114, No. 5, Feb. 1992, pp. 1895–1897.

Kim Dueholm et al., "Synthesis of Peptide Nucleic Acid Monomers Containing the Four Natural Nucleobases. Thymine, Cytosine, Adenine, and Guanine and their Oligomerization," vol. 59, No. 19, Sep. 1994, pp. 5767–5773.

Heimer et al., "Synthesis of Analogs and Oligomers of N–(2–aminoethyl) glycine and their Gastrointestinal Absorption in the Rat", Int. J. Peptide Protein Res. 23, (1984) pp. 203–211.

Egholm et al., "Recognition of Guanine and Andenine in DNA by Cytosine and Thymine Containing Peptide Nucleic Acids (PNA)", J. Am. Chem. Soc., 114, (1992) pp. 9677–9678.

Merrifield, "Solid Phase Peptide Synthesis. I. The Synthesis of a Tetrapeptide", J. Am. Chem. Soc., 85, (1963) pp. 2149–2154.

Kohda et al., "Synthesis and Properties of N–Aminopyrimidines", Tetrahedron, vol. 49, 19, (1993) pp. 3947–3958.

Castro et al., "Reactifs De Couplage Peptidique IV", Tetrahedron Letters, 14, (1975) pp. 1219–1222.

Coste et al., "PyBOP®: A New Peptide Coupling Reagent Devoid of Toxic By–Product", Tetrahedron Letters, vol. 31, 2, (1990), pp. 205–208.

Coste et al., "BROP: A New Reagent for Coupling N–Methylated Amino Acids", Tetrahedron Letters, vol. 31, 5, (1990) pp. 669–672.

Coste et al., "Oxybenzotriazole Free Peptide Coupling Reagents for N–Methylated Amino Acids", Tetrahedron Letters, vol. 32, 17, (1991) pp. 1967–1970.

Dourtoglou et al., "O–Benzotriazolyl–N,N,N', N'–tetramethyluronium Hexafluorophosphate As Coupling Reagent for the Synthesis of Peptides of Biological Interest", Synthesis, (1984) pp. 572–574.

Knorr et al., "New Coupling Reagents in Peptide Chemistry", Tetrahedron Letters, (1989) pp. 1927–1930.

Carpino, "1–Hydroxy–7–Azabenzotriazole. An Efficient Peptide Coupling Additive", J. Am. Chem. Soc., 115, (1993) pp. 4397–4398.

Ehrlich et al., "Synthesis of Cyclic Peptides Via Efficient New Coupling Reagents", Tetrahedron Letters, vol. 34, 30, (1993) pp. 4781–4784.

Akaji et al., "Anchoring of Fmoc Amino Acid to 4–Alkoxybenzyle Alcohol Resin Using a New Esterification Reagent", Tetrahedron Letters, vol. 33, 22, (1992) pp. 3177–3180.

Blankemeyer–Menge et al., "An Efficient Method for Anchoring Fmoc–Amino Acids to Hydroxyl–Functionalised Solid Supports," Tetrahedron Letters, vol. 21, 12, (1990) pp. 1701–1704.

Kirstgen et al., "Use of Esters of 2,5–Diphenyl–2, 3–dihydro–3–oxo–4–hydroxythiophene Dioxide in Solid Phase Peptide Synthesis. A New Procedure for Attachment of the First Amino Acid", J. Chem. Soc., Chem. Commun. (1987) pp. 1870–1871.

Hudson et al., "Methodological Implications of Simultaneous Solid–Phase Peptide Synthesis: A Comparison of Active Esters", Peptide Research, vol. 3, 1, (1990) pp. 51–55.

JCBN "Nomenclature and Symbolism for Amino Acids and Peptides", Eur. J. Biochem., 138, (1984) pp. 9–37.

* cited by examiner

SUBSTITUTED N-ETHYLGLYCINE DERIVATIVES FOR PREPARING PNA AND PNA/DNA HYBRIDS

This is a division of application Ser. No. 08/402,840, filed Mar. 13, 1995, which is incorporated herein by reference now U.S. Pat. No. 6,075,143.

Substituted N-ethylglycine derivatives for preparing PNA and PNA/DNA hybrids

The present invention relates to novel substituted N-ethylglycine derivatives for preparing PNA and PNA/DNA hybrids as described in the simultaneously filed application "Peptide oligonucleotide derivatives, their preparation and their use" (HOE 94/F 057, DE-P 44 08 534.6)

Peptide or polyamide nucleic acids (PNA) are DNA-analogous compounds, in which the deoxyribose phosphate backbone was replaced by a peptide oligomer. The syntheses hitherto described in the literature (for example Michael Egholm, Peter E. Nielsen, Rolf H. Berg and Ole Buchardt, Science 1991, 254, 1497–1500; Ole Buchardt, Michael Egholm, Peter E. Nielsen and Rolf H. Berg, WO 92/20702) use, as a temporary protective group for the amino group of the monomer, the acid-labile tert-butyloxycarbonyl (Boc) protective group, which is eliminated by medium-strong acids such as, for example, trifluoroacetic acid. The solid-phase synthesis of oligomers is carried out in accordance with the customary peptide synthesis processes, as they have been described, for example, by Merrifield (B. Merrifield, J. Am. Chem. Soc., 1963, 85, 2149). The PNA oligomer is eliminated with the aid of a strong acid, customarily using liquid hydrogen fluoride.

The repeated treatment with trifluoroacetic acid and the subsequent cleavage using hydrogen fluoride is not compatible with the synthesis of mixed PNA/DNA sequences, since the nucleosidic linkage is not stable under these conditions. In particular, the purine nucleotides deoxyguanosine and deoxyadenosine are rapidly cleaved on the N-glycosidic linkage by strong acids. Moreover, it would be particularly desirable for the synthesis of such molecules to use the customary DNA synthesizers and to largely retain the chemistry used in this apparatus. This also applies to the preparation of PNA sequences with the aid of such apparatus.

It is therefore an aim of the invention to provide glycine derivatives which allow a simple construction of PNA and PNA/DNA hybrids as well as the use of automatic synthesizers.

Substances which are suitable for this purpose are the compounds of the formula I

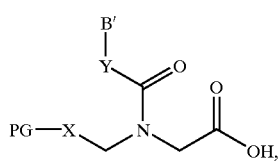

(I)

in which

PG is a urethane-type amino protective group which is labile to weak acids, such as, for example, 1-(1-adamantyl)1-methylethoxycarbonyl (Adpoc), 1-(3,5-di-tert-butylphenyl)1-methylethoxycarbonyl (t-Bumeoc) and 1-methyl-1-(4-biphenyl)ethyloxycarbonyl (Bpoc), 3,5-dimethoxyphenyl-2-propyl-2-oxycarbonyl (Ddz), or a trityl-type amino protective group which is labile to weak acids, such as triphenyl (Trt), (4-methoxyphenyl)diphenylmethyl (Trt), (4-methylphenyl)diphenylmethyl (Mtt), di-(4-methoxyphenyl)phenylmethyl (Dmt) and 9-(9-phenyl)xanthenyl (pixyl), X is NH, O or S, preferably NH or O, Y is $CH_2$, NH or O, preferably $CH_2$, and B' are bases customary in nucleotide chemistry, for example natural bases, such as adenine, cytosine, guanine, thymine and uracil, or unnatural bases, such as purine, 2,6-diaminopurine, 7-deazaadenine, 7-deazaguanine, $N^4N^4$-ethanocytosine, $N^6N^6$-ethano-2,6 diaminopurine, 5-methylcytosine, 5-($C_3$–$C_6$)-alkynyluracil, 5-($C_3$–$C_6$)alkynylcytosine, 5-fluorouracil and pseudoisocytosine, the exocyclic amino or hydroxyl groups of all of these being protected by suitable known protective groups, such as the benzoyl, isobutanoyl, acetyl, phenoxyacetyl, 4-(t-butyl)benzoyl, 4-(t-butyl)phenoxyacetyl, 4-(methoxy)benzoyl, 2-(4-nitrophenyl)ethyloxycarbonyl, 2-(2,4-dinitrophenyl)ethyloxycarbonyl, 9-fluorenylmethoxycarbonyl, diphenylcarbamoyl or formamidine group, preferably the benzoyl, isobutanoyl, acetyl, phenoxyacetyl, 4-(tbutyl)benzoyl or 4-(methoxy)benzoyl group, and also, in the case of guanine, by a combination of 2-N-acetyl with 6-O-diphenylcarbamoyl, or are base substitute compounds, such as, for example, imidazole, triazole or nitroimidazole, and their salts, preferably their salts with tertiary organic bases, such as, for example, triethylamine or pyridine.

Compounds of the formula I where Y is $CH_2$ can be obtained, for example, by reacting a compound of the formula II
in which
PG and X are as defined above and,
$R^1$ is hydrogen or an ester protective group, such as, for example, methyl, ethyl, butyl or 2-(methoxyethoxy) ethyl,
with a compound of the formula III

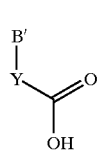

(III)

in which
B' is as defined above and
Y is $CH_2$
at 0–45° C., preferably at room temperature, in a suitable solvent, such as, for example, DMF, acetonitrile, dichloromethane or mixtures of these solvents, using a coupling reagent conventionally used in peptide chemistry, such as, for example, carbodiimides, phosphonium reagents, uronium reagents, acid halides or activated esters, to give a compound of the formula IV

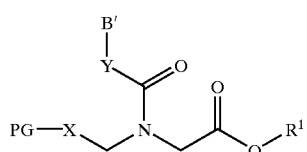

(IV)

in which PG, X, B' and $R^1$ are as defined above and subsequently converting this compound to a compound of the formula I by eliminating the ester protective group $R^1$ under weakly alkaline conditions using alkali metal hydroxide solution, such as, for example, NaOH, LiOH, KOH, or by tertiary amine compounds in water, such as, for example, triethylamine, or else enzymatically with the aid of esterases or lipases at 0–50° C., preferably at room temperature, in a suitable solvent, such as dioxane, water, tetrahydrofuran, methanol, water or mixtures of the solvents.

Activation methods conventionally used in peptide synthesis are described, for example, in Houben-Weyl, Methoden der organischen Chemie [Methods in organic Chemistry], Volume 15/2, Georg Thieme Verlag Stuttgart 1974, or further reagents are described in the particular references, for example BOP (B. Castro, J. R. Dormoy, G. Evin and C. Selve, Tetrahedron Lett. 1975, 1219–1222), PyBOP (J. Coste, D. Le-Nguyen and B. Castro, Tetrahedron Lett. 1990, 205–208), BroP (J. Coste, M.-N. Dufour, A. Pantaloni and B. Castro, Tetrahedron Lett. 1990, 669–672), PyBroP (J. Coste, E. Frerot, P. Jouin and B. Castro, Tetrahedron Lett. 1991, 1967–1970) and uronium reagents, such as, for example, HBTU (V. Dourtoglou, B. Gross, V. Lambropoulou, C. Zioudrou, Synthesis 1984, 572–574), TBTU, TPTU, TSTU, TNTU, (R. Knorr, A. Trzeciak, W. Bannwarth and D. Gillessen, Tetrahedron Letters 1989, 1927–1930), TOTU (EP-A-0 460 446), HATU (L. A. Carpino, J. Am. Chem. Soc. 1993, 115, 4397–4398), HAPyU, TaPipU (A. Ehrlich, S. Rothemund, M. Brudel, M. Beyermann, L. A. Carpino and M. Bienert, Tetrahedron Lett. 1993, 4781–4784), BOI (K. Akaji, N. Kuriyama, T. Kimura, Y. Fujiwara and Y. Kiso, Tetrahedron Lett. 1992, 3177–3180) or acid chlorides or acid fluorides (L. A. Carpino, H. G. Chao, M. Beyermann and M. Bienert, J. Org. Chem., 56(1991), 2635; J.-N. Bertho, A. Loffet, C. Pinel, F. Reuther and G. Sennyey in E. Giralt and D. Andreu (Eds.) Peptides 1990, Escom Science Publishers B. V. 1991, pp. 53–54; J. Green and K. Bradley, Tetrahedron 1993, 4141–4146), 2,4,6-mesitylenesulfonyl-3-nitro-1,2,4-triazolide (MSNT) (B. Blankemeyer-Menge, M. Nimitz and R. Frank, Tetrahedron Lett. 1990, 1701–1704), 2,5-diphenyl-2,3-dihydro-3-oxo-4-hydroxythiophene dioxide (TDO) (R. Kirstgen, R. C. Sheppard, W. Steglich, J. Chem. Soc. Chem. Commun. 1987, 1870–1871) or activated esters (D. Hudson) Peptide Res. 1990, 51–55).

Preferred is the use of carbodiimides, for example dicyclohexylcarbodiimide or diisopropylcarbodiimide. Other reagents which are preferably used are phosphonium reagents, such as, for example, PyBOP or PbBroP, uronium reagents, such as, for example HBTU, TBTU, TPTU, TSTU, TNTU, TOTU or HATU, BOI or acid chlorides or acid fluorides.

To synthesize the compounds of the formula II, aminoethylglycine, hydroxyethylglycine, mercaptoethylglycine or their corresponding esters are provided with the corresponding protective group which is labile to weak acids. The protective group which is labile to weak acids is introduced with the aid of processes per se known from the literature, some of which have been modified. Examples of suitable reagents are t-Bumeoc fluoride, Adpoc azide, Bpoc azide, Ddz (phenyl)carbonate, Trt Cl, Mtt Cl, Mmt Cl, Mmt Cl, Dmt Cl, Pixyl Cl. In this reaction, the solubility of the aminoethylglycine can be improved while simultaneously protecting the acid function by reacting it with customary silylation reagents, such as, for example, bis-trimethylsilylacetamide. After the reaction with the protective group reagents, this temporary protective group is eliminated by adding water or alcohols to the reaction mixture. The aminoethylglycine or the corresponding aminoethylglycine ester used as the starting material are prepared by a method known from the literature (E. P. Heimer, H. E. Gallo-Torres, A. M. Felix, M. Ahmad, T. J. Lambros, F. Scheidl and J. Meienhofer, Int. J. Peptide Protein Res. 23, 1984, 203–211) 2-aminoethylglycine (H-Aeg-OH).

A further process for the preparation of aminoethylglycine consists in subjecting glyoxylic acid to reductive amination with ethylene diamine and is described in the application titled "Process for the preparation of aminoethylglycine" (HOE 94/F 061, DE-P 44 08 530.3) filed simultaneously.

2-Hydroxyethylglycine or 2-mercaptoethylglycine is synthesized, for example, by subjecting glyoxylic acid or glyoxylic esters to reductive amination with aminoethanol or cysteamine using hydrogen on palladium-on-charcoal or, in the case of 2-mercaptoethylglycine, preferably using sodium cyanoborohydride or sodium triacetoxyborohydride as the reducing agent.

The compound of the formula I, which is derived from 2-mercaptoethylglycine, can also be obtained by first reacting 2-mercaptoethylamine or its hydrochloride with the corresponding triphenyl derivative, such as, for example, its halides or alcohols, in acetic acid or mixtures of acetic acid/water. Under the acidic conditions, the reaction is preferably effected on the sulfur of 2-mercaptoethylamine via the corresponding trityl cation. The use of (4-methoxyphenyl)diphenylmethyl chloride is preferred for introducing the Mmt group, and the use of di-(4-methoxyphenyl)phenylmethyl chloride for introducing the Dmt group. The amino group is subsequently alkylated by reaction with haloacetic esters, preferably bromoacetic esters, using an organic auxiliary base, such as, for example, diisopropyl ethyl amine, in a suitable solvent, such as, for example, DMF. The resulting compound of the formula II in which PG is a trityl-type protective group, X is S and $R^1$ is an ester protective group can then be reacted in the manner described above to give the corresponding compounds of the formula I.

The acetic acid derivatives of the nucleobases, of the formula III, can be retained by alkylating the corresponding nucleobases or the nucleobases which are protected in the exocyclic hydroxyl or amino function using chloroacetic acid, bromoacetic acid, iodoacetic acid, or their esters. For preference, temporary protective groups are additionally introduced on the nucleobase for the purposes of selective alkylation. Protective groups which are suitable for the nucleobases are all protective groups which are compatible with the protective group PG which is labile to weak acids. Protective groups which are preferably used for the exocyclic amino function are, for example, the benzoyl, isobutanoyl, acetyl, phenoxyacetyl, 4-(t-butyl)benzoyl, 4-(t-butyl)phenoxyacetyl, 4-(methoxy)benzoyl, 2-(4-nitrophenyl)ethyloxycarbonyl, 2(2,4-dinitrophenyl) ethyloxycarbonyl, 9-fluorenylmethoxycarbonyl, diphenylcarbamoyl, or formamidine group.

Particularly preferred are the benzoyl, isobutanoyl, 4-(t-butyl)benzoyl, 2-(4-nitrophenyl)ethyloxycarbonyl, 2(2,4-dinitrophenyl)ethyloxycarbonyl, 9-fluorenylmethoxycarbonyl, 4-(methoxy)benzoyl or para-(t-butyl)phenoxyacetyl or para-nitrophenyl-2-ethyloxycarbonyl group and, in the case of guanine, a combination of the 2-N-acetyl with the 6-O-diphenylcarbamoyl group.

An alternative process for the preparation of the compounds of the formula I in which Y is $CH_2$ consists in reacting a compound of the formula II

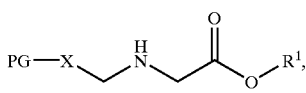
(II)

in which
   PG and X are as defined above and
   $R^1$ is hydrogen or a temporary silyl protective group, such as, for example, trimethylsilyl,
with a compound of the formula V

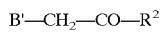
B'—CH$_2$—CO—R$^2$       (V), in which
   B' is as defined above and
   $R^2$ is halogen, such as, for example, fluorine, chlorine or bromine, or the radical of an active ester, such as, for example, OBt, OObt, OPfp, ONSu,
at 0–40° C., preferably 20–30° C., in a suitable solvent, such as, for example, DMF, NMP, acetonitrile, dichloromethane or mixtures of these solvents, it optionally being possible to protect the acid function in the compound of the formula II temporarily by reacting it with customary silylation reagents, such as, for example, bis-trimethylsilylacetamide, and to eliminate these temporarily protective groups—after the reaction with the compound of the formula V—by adding water or alcohols to the reaction mixture.

A further alternative process for the preparation of the compounds of the formula I where Y is CH$_2$ consists in reacting
a compound of the formula II

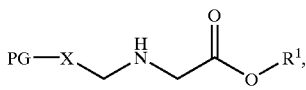
(II)

in which
   PG and X are as defined above and
   $R^1$ is an ester protective group, such as, for example, methyl, ethyl, butyl, 2-(methoxyethoxy)ethyl and the like,
with a haloacetic acid derivative, such as, for example, chloroacetyl chloride, bromoacetyl bromide, bromoacetyl chloride or iodoacetyl chloride, in a suitable solvent, such as, for example, tetrahydrofuran, dichloromethane or DMF, using an auxiliary base, such as, for example, triethylamine, N-ethylmorpholine or diisopropylethylamine, to give the compound of the formula VI

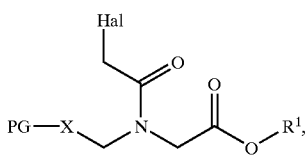
(VI)

in which
   Hal is Cl, Br or I, preferably Br or Cl, very particularly Cl, and
   PG, X and R are as defined above,
reacting this intermediate of the formula VI with the optionally protected nucleobase B' and an auxiliary base, for example potassium carbonate, in a suitable solvent, for example DMF or NMP, to give the compound of the formula IV

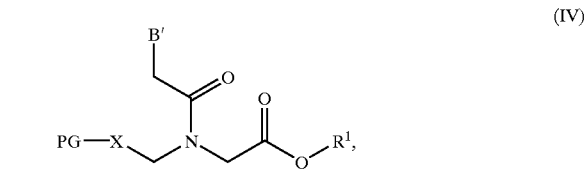
(IV)

and subsequently converting this compound to a compound of the formula I by eliminating the ester protective group $R^1$ using alkali metal hydroxide solution, such as, for example, NaOH, LiOH or KOH, or else enzymatically with the aid of esterases or lipases at 0–50° C., preferably at room temperature, in a suitable solvent, such as dioxane, water, tetrahydrofuran, methanol, water or mixtures of these solvents.

Compounds of the formula I in which Y is o or NH are obtained by reacting
a compound of the formula II

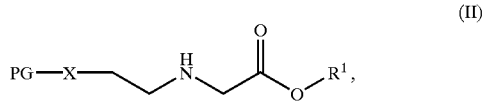
(II)

in which
   PG and X are as defined above and
   $R^1$ is an ester protective group, such as, for example, methyl, ethyl, butyl or 2-(methoxyethoxy)ethyl, or a temporary ester protective group, such as, for example, trimethylsilyl,
with a compound of the formula VII

B'—Y—CO—R$^3$       (VII)

in which
   B' is as defined above,
   Y is O or NH and
   $R^3$ is Cl, ONp or ONSu
at 0–40° C., preferably 20–30° C., in a suitable solvent, such as DMF, acetonitrile or dichloromethane, or mixtures of these solvents, and subsequently eliminating the ester protective group $R^1$ using alkali metal hydroxide solution, such as, for example, NaOH, LiOH or KOH, or else enzymatically with the aid of esterases or lipases at 0–50° C., preferably at room temperature, in a suitable solvent, such as dioxane, water, tetrahydrofuran, methanol, water or mixtures of these solvents.

The N-amino- or N-hydroxy-nucleobases required as starting material for this latter reaction are obtained by known processes, such as, for example, as described by K. Kohda, I. Kobayashi, K. Itano, S. Asano, Y. Kawazoe (Tetrahedron 49, 3947–3958 (1993)) and then reacted with phosgene or chloroformic esters to give the carbamates or carbonates of the formula VII.

The abbreviations used for amino acids correspond to the three-letter code conventionally used in peptide chemistry, as it is described in Europ. J. Biochem. 138, 9 (1984). Other abbreviations used are listed hereinbelow.

| | |
|---|---|
| Aeg | N-(2-aminoethyl)glycyl, —NH—CH$_2$—CH$_2$—NH—CH$_2$—CO— |
| Aeg(A$^{MeOBz}$) | N-(2-aminoethyl)-N-((9-(N$^6$-4-methoxy-benzoyl)adenosyl)acetyl)glycyl |
| Aeg(C$^{Bz}$) | N-(2-aminoethyl)-N-((1-(N$^4$-benzoyl)-cytosyl)acetyl)glycyl |
| Aeg(C$^{MeOBz}$) | N-(2-aminoethyl)-N-((1-(N$^4$-4-methoxyben-zoyl)cytosyl)acetyl)glycyl |
| Aeg(C$^{tBuBz}$) | N-(2-aminoethyl)-N-((1-(N$^4$-4-tert-butyl-benzoyl)cytosyl)acetyl)glycyl |
| Aeg(G$^{iBu}$) | N-(2-aminoethyl)-N-((9-(N$^2$-isobutanoyl)-guanosyl)acetyl)glycyl |
| Aeg(G$^{2-Ac,4-Dpc}$) | N-(2-aminoethyl)-N-((9-(N$^2$-acetyl-O$^4$-di-phenylcarbamoyl)guanosyl)glycyl |
| Aeg(Im) | N-(2-amino)ethyl-N-((1-imidazoyl)-acetyl)glycyl |
| Aeg(Im$^{4-Nitro}$) | N-(2-aminoethyl)-N-((1-(4-nitro)imida-zolyl)acetyl)glycyl |
| Aeg(T) | N-(2-aminoethyl)-N-((1-thyminyl)acetyl)-glycyl |
| Aeg(Triaz) | N-(2-aminoethyl)-N-((1-(1,2,4)tri-azoyl)acetyl)glycyl |
| Bnpeoc | 2,2-[bis(4-nitrophenyl)]ethoxycarbonyl) |
| Boc | tert-butyloxycarbonyl |
| BOI | 2-(benzotriazol-1-yl)oxy-1,3-dimethyl-imidazolidinium hexafluorophosphate |
| BOP | benzotriazoyl-1-oxy-tris(dimethyl-amino)-phosphonium hexafluorophosphate |
| BroP | bromotris(dimethylamino)phosphonium hexafluorophosphate |
| BSA | N,O-bis-(trimethylsilyl)acetamide |
| But | tert-butyl |
| Bz | benzoyl |
| Bzl | benzyl |
| Cl—Z | 4-chlorobenzyloxycarbonyl |
| CPG | controlled pore glass |
| DBU | 1,8-diazabicyclo[5.4.0]undec-7-ene |
| DCM | dichloromethane |
| Ddz | 3,5-dimethoxyphenyl-2-propyl-2-oxycarbonyl |
| DMF | dimethylformamide |
| Dmt | di-(4-methoxyphenyl)phenylmethyl |
| Dnpeoc | 2-(2,4-dinitrophenyl)ethoxycarbonyl |
| Dpc | diphenylcarbamoyl |
| FAM | flourescein radical |
| Fm | 9-fluorenylmethyl |
| Fmoc | 9-fluorenylmethyloxycarbonyl |
| H—Aeg—OH | N-(2-aminoethyl)glycine |
| HAPyU | O-(7-Azabenzotriazol-1-yl)-1,1,3,3-bis-(tetramethylene)uronium hexafluorophosphate |
| HATU | O-(7-azabenzotriazol-1-yl)-1,1,3,3-tetramethyluronium hexafluorophosphate |
| HBTU | O-(benzotriazol-1-yl)-1,1,3,3-tetra-methyluronium hexafluorophosphate |
| HOBt | 1-hydroxybenzotriazole |
| HONSu | N-hydroxysuccinimide |
| HOObt | 3-hydroxy-4-oxo-3,4-dihydrobenzotriazine |
| iBu | isobutanoyl |
| MeOBz | 4-methoxybenzoyl |
| Mmt | 4-methoxytriphenylmethyl |
| Moz | 4-methoxybenzyloxycarbonyl |
| MSNT | 2,4,6-mesitylenesulfonyl-3-nitro-1,2,4-triazolide |
| Mtt | 4-methylphenyl)diphenylmethyl |
| NBA | nitrobenzyl alcohol |
| NMP | N-methylpyrrolidine |
| Oeg | N-(2-oxyethyl)glycyl, —O—CH$_2$—CH$_2$—NH—CH$_2$—CO— |
| Pixyl | 9-(9-phenyl)xanthenyl |
| PyBOP | benzotriazolyl-1-oxy-tripyrrolidinophos-phonium hexafluorophosphate |
| PyBroP | bromotripyrrolidinophosphonium hexa-fluorophosphate |
| TAPipU | O-(7-azabenzotriazol-1-yl)-1,1,3,3-bis-(pentamethylene)uronium tetrafluoroborate |
| TBTU | O-(benzotriazol-1-yl)-1,1,3,3-tetra-methyluronium tetrafluoroborate |
| tBu | tert-butyl |
| tBuBz | 4-tert-butylbenzoyl |
| TDBTU | O-(3,4-dihydro-4-oxo-1,2,3-benzotriazin-3-yl)-1,1,3,3-tetramethyluronium tetrafluoroborate |
| TDO | 2,5-diphenyl-2,3-dihydro-3-oxo-4-hydroxy-thiophenedioxide |
| Teg | N-(2-thioethyl)glycyl, —S—CH$_2$—CH$_2$—NH—CH$_2$—CO— |
| TFA | trifluoroacetic acid |
| THF | tetrahydrofuran |
| TNTU | O-[(5-norbonene-2,3-dicarboximido]-1,1,3,3-tetramethyluronium tetrafluoroborate |
| TOTU | O-[(cyano(ethoxycarbonyl)methylene)-amino]-1,1,3,3-tetramethyluronium tetrafluoroborate |
| TPTU | O-(1,2-dihydro-2-oxo-1-pyridyl)-1,1,3,3'-tetramethyluronium tetrafluoroborate |
| Trt | trityl |
| TSTU | O-(N-succinimidyl)-1,1,3,3-tetramethyl-uroniumtetrafluoroborate |
| Z | benzyloxycarbonyl |
| MS(ES$^+$) | electrostatic spraying mass spectrum (positive ion) |
| MS(ES$^-$) | electrostatic spraying mass spectrum (negative ion) |
| MS(DCI) | desorption chemical ionization mass spectrum |
| MS(FAB) | Fast Atom Bombardment mass spectrum |

EXAMPLES

Example 1

Preparation of N-(Hydroxyethyl)glycine
H-Oeg-OH 46 g of glyoxylic acid monohydrate are dissolved in 1,000 ml of water, and 30.2 ml of 2-aminoethanol are then added with stirring and cooling. The mixture is treated with 10 g of catalyst (10% Pd/C) and hydrogenated in the autoclave at room temperature and a hydrogen pressure of bar. For working up, the catalyst is filtered off with suction and the filtrate is concentrated to dryness in vacuo. The residue is subjected to two distillations using a small amount of toluene. This crude product is digested using 250 ml of hot methanol, filtered off with suction while warm, washed with a small amount of methanol and then dried in a desiccator.

Yield: 49.56 g; M.p.: 178–180° C., decomposition; R$_f$=0.36 (n-butanol/acetic acid/water/ethyl acetate 1:1:1:1); MS(DCI): 120 (M+H)$^+$.

Example 2

Synthesis of N-(9-Fluorenylmethoxycarbonyl)-N-(hydroxyethyl)glycine
H-Oeg(Fmoc)-OH 10.08 g of sodium hydrogen carbonate are dissolved in 150 ml of water, and 7.15 g of N-(hydroxyethyl)glycine are then added with stirring. After approximately 5 minutes, a clear solution is obtained, and 20.22 g of Fmoc-ONSu in 300 ml of dioxane are added dropwise with vigorous stirring. Stirring is continued for 3 hours at room temperature and the mixture is then allowed to stand overnight at 4° C. The solution is filtered and the filtrate is concentrated in vacuo on a rotary evaporator. The residue is taken up in 100 ml of water and the pH is brought to 2 by adding portions of potassium hydrogen sulfate solution. The mixture is then extracted three times using in each case 150 ml of ethyl acetate, the organic phase is washed four times using in each case 50 ml of water and dried over sodium sulfate. The desiccant is filtered off, and the filtrate is concentrated to dryness in vacuo on a rotary evaporator. The residue is treated with 200 ml of diisopropyl ether and triturated, which results in crystallization. The mixture is allowed to stand overnight, and the precipitate is filtered off with suction and recrystallized from ethyl acetate/diisopropyl ether. The resulting product is filtered off with suction and dried in a desiccator.

Yield: 15.8 g; M.p.: 114–116° C., decomposition. $R_f$=0.62 (n-butanol/acetic acid/water 3:1:1); MS(ES$^+$): 342 (M+H)$^+$.

Example 3

Synthesis of N-(9-Fluorenylmethoxycarbonyl)-N-(4-methoxyphenyldiphenylmethoxyethyl)glycine Mmt-Oeg(Fmoc)-OH 14.74 g of N-(fluorenylmethoxycarbonyl)-N-(hydroxyethyl)glycine are dissolved in 160 ml of pyridine, and 13.31 g of 4-methoxyphenyldiphenylmethyl chloride are added. The mixture is stirred for 2 hours at room temperature and allowed to stand overnight at 4° C. The solvent is then stripped off in vacuo on a rotary evaporator, the residue is taken up in 300 ml of ethyl acetate, and the mixture is extracted three times using in each case 30 ml of saturated aqueous bicarbonate solution. The extracts are then also washed three times using in each case 30 ml of water, and the organic phase is dried over sodium sulfate. The desiccant is filtered off, and the filtrate is concentrated to a volume of approximately 70 ml and added dropwise with stirring to 700 ml of diisopropyl ether. The product which has precipitated is filtered off with suction and dried in a desiccator.

Yield: 19.95 g; $R_f$=0.45 (ethyl acetate/methanol/triethylamine=60:40:1); MS(FAB/MeOH/NBA): 658.3 (M+2Na)$^+$.

Example 4

$N^4$-(4-Methoxybenzoyl)cytosine

Example 4a

Cytosine (11.1 g) is suspended in dry pyridine (250 ml). Using a syringe, 4-methoxybenzoyl chloride (17.06 g) is then added dropwise. A virtually clear solution is formed from which a precipitate separates out after approximately 10 minutes. stirring is continued for approximately 1.5 hours at room temperature, and the precipitate is then filtered off. The precipitate is the desired product.

Yield: 20.5 g; MS(ES$^+$): 246 (M+H)$^+$; $R_f$=0.77 (dichloromethane:isopropanol/8:2).

Example 4b

Cytosine (2.8 g) is suspended in dry DMF (100 ml) and treated with triethylamine (2 ml). Using a syringe, 4-methoxybenzoic anhydride (7.2 g) is then added dropwise. A virtually clear solution is formed from which a precipitate separates out after some time. stirring is continued for approximately 2 hours at room temperature, and the precipitate is then filtered off. The precipitate is the desired product.

Yield: 5.9 g; MS(ES$^+$): 246 (M+H)$^+$; $R_f$=0.77 (dichloromethane:isopropanol/8:2).

Example 5

$N^4$-(4-Methoxybenzoyl)-N'-methoxycarbonylmethylcystosine $N^4$-(4-Methoxybenzoyl)cytosine (12.25 g) is suspended in dry DMF (250 ml), and sodium hydride (1.25 g) is added in portions. The mixture is heated briefly at 60° C. until the evolution of hydrogen has ceased. Methyl bromoacetate (4.75 ml) is subsequently added dropwise at room temperature using a syringe. stirring is continued for 1 hour at room temperature, and the mixture is then treated with a small amount of carbon dioxide in methanol. The solvent is stripped off in vacuo, and the residue which remains is treated with dichloromethane and then filtered. The filter residue is also washed with a small amount of water and then dried in vacuo.

Yield: 12.86 g; M.p.: 219° C.; MS(ES$^+$): 318 (M+H)$^+$; $R_f$=0.71 (n-butanol:acetic acid:water/3:1:1).

Example 6

$N^4$-(4-Methoxybenzoyl)-$N^1$-carboxymethylcytosine $N^4$-(4-Methoxybenzoyl)-$N^1$-methoxycarbonylmethylcytosine (12.5 g) is suspended in water (100 ml) and 2N aqueous sodium hydroxide solution is added dropwise at 0° C. while the pH is checked (pH 12) until the methyl ester is hydrolyzed. The course of the reaction is monitored by means of TLC. The reaction solution is then filtered, and the pH of the filtrate is brought to 3 using 2M potassium hydrogen sulfate solution, during which process the product precipitates. The precipitate is filtered off, washed with a small amount of cold water and dried in vacuo.

Yield: 11.5 g; M.p.: 270–275° C., decomposition; MS(ES$^+$): 304 (M+H)$^+$; $R_f$=0.53 (n-butanol:acetic acid:water/3:1:1).

Example 7

$N^4$-(4-tert-Butylbenzoyl)cytosine

Cytosine (11.1 g) is suspended in dry DMF (250 ml), and triethylamine (15.4 ml) is added. 4-tert-Butylbenzoyl chloride (18.6 ml) is then added dropwise using a syringe. stirring is then continued for approximately 4 hours at room temperature and more 4-tert-butylbenzoyl chloride (3.7 ml) is then added. After a further 2 hours, the reaction is quenched by adding a small amount of methanol. The solvent is removed in vacuo, and the residue is treated with dichloromethane and water. The solid which precipitates in this process is the desired substance. The precipitate is filtered off and dried in vacuo.

Yield: 15.7 g; MS(DCI): 272 (M+H)$^+$; $R_f$=0.55 (dichloromethane:methanol/9:1).

Example 8

$N^4$-(4-tert-Butylbenzoyl)-$N^1$-methoxycarbonylmethylcytosine $N^4$-(4-tert-Butylbenzoyl)cytosine (14.96 g) is suspended in dry DMF (250 ml), sodium hydride (1.32 g) is added in portions, and the mixture is stirred for 1 hour at room temperature until the evolution of hydrogen has ceased. Methyl bromoacetate (5.2 ml) is subsequently added dropwise at room temperature using a syringe. Stirring is continued for 1 hour at room temperature, and methanol (10 ml) is then added. The solvent is stripped off in vacuo, and the residue which remains is partitioned between dichloromethane and water. The organic phase is washed with water, dried over sodium sulfate, filtered and then concentrated in vacuo. The resulting crude product is recrystallized from isopropanol and then dried in vacuo.

Yield: 8.0 g; M.p.: 189–193° C., decomposition; MS(DCI): 344 (M+H)$^+$; $R_f$=0.72 (dichloromethane:methanol/9:1).

Example 9

$N^4$-(4-tert-Butylbenzoyl)-$N^1$-carboxymethylcytosine $N^4$-(4-tert-Butylbenzoyl)-$N^1$-methoxycarbonylmethylcytosine (8.0 g) is dissolved in a mixture of dioxane (50 ml) and water (10 ml), and 2N aqueous sodium hydroxide solution is added dropwise with stirring at room temperature (pH 11–12). When hydrolysis of the methyl ester is complete—TLC check —, the pH of the reaction solution is brought to 3 using 2M potassium hydrogen sulfate solution. The precipitate which has separated out is filtered off with suction. This crude product is dissolved in sodium carbonate solution and reprecipitated by adding 2M potassium hydrogen sulfate solution. The product is filtered off with suction, washed with a small amount of water and dried in vacuo.

Yield: 6.62 g; M.p.: from 285° C., decomposition; MS(DCI): 330 (M+H)$^+$; $R_f$=0.2 (dichloromethane:methanol/9:1).

Example 10

$N^4$-(Benzoyl)cytosine

Cytosine (5.55 g) is suspended in dry pyridine (100 ml). Using a syringe, benzoyl chloride (6.4 ml) is then added dropwise. A virtually clear solution is formed from which a precipitate separates out after approximately 5 minutes. Stirring is continued for approximately 2 hours at room temperature, methanol (100 ml) is then added, and the mixture is concentrated in vacuo. The residue is stirred with isopropanol, filtered, washed with a small amount of methanol and diethyl ether, and dried in vacuo.

Yield: 10.1 g; M.p.:<305° C.; MS(DCI): 216 (M+H)$^+$.

Example 11

$N^4$-(Benzoyl)-$N^1$-methoxycarbonylmethylcytosine $N^4$-(Benzoyl)cytosine (4.3 g) is suspended in dry DMF (60 ml), and sodium hydride (0.48 g) is added in portions). The mixture is heated briefly at 40° C. until the evolution of hydrogen has ceased. Methyl bromoacetate (2.1 ml) is subsequently added dropwise at room temperature, using a syringe. Stirring is continued for 2.5 hours at room temperature, and the mixture is then treated with methanol (10 ml). The solvent is stripped off in vacuo, and the residue which remains is treated with dichloromethane and then filtered. The filter residue is also washed with a small amount of water and then dried in vacuo.

Yield: 6.45 g; M.p.: 234° C.; MS(DCI): 288 (M+H)$^+$; $R_f$=0.85 (ethyl acetate:methanol/8:2).

Example 12

$N^4$-(Benzoyl)-$N^1$-carboxymethylcytosine $N^4$-(Benzoyl)-$N^1$-methoxycarbonylmethylcytosine (5.85 g) is dissolved in a mixture of dioxane (80 ml) and water (40 ml) and 2N aqueous sodium hydroxide solution (11.25 ml) is added dropwise at room temperature, with stirring (pH 11–12). When hydrolysis of the methyl ester is complete— TLC check—, the pH of the reaction solution is brought to 3 using 2M potassium hydrogen sulfate solution. The precipitate which has separated out is filtered off with suction. This crude product is dissolved in sodium carbonate solution and reprecipitated by adding 2M potassium hydrogen sulfate solution. The product is filtered off with suction, washed with a small amount of water and dried in vacuo.

Yield: 5.84 g; M.p.: from 283–286° C., decomposition; MS(ES$^+$): 274 (M+H)$^+$; $R_f$=0.15 (ethyl acetate:methanol/8:2).

Example 13

$N^4$-(tert-Butyloxycarbonyl)cytosine

Cytosine (11.1 g) is suspended in dry pyridine (250 ml). Di-tert-butyl dicarbonate (21.8 g) and 1 spatula-tipful of 4-dimethylaminopyridine are then added. The mixture is stirred for 6 hours at 60° C., during which process a dense precipitate is formed. The reaction solution is cooled, and the precipitate is filtered off with suction. The precipitate is stirred with water under hot conditions, filtered off with suction and dried in vacuo.

Yield: 10.26 g; MS(DCI): 212 (M+H)$^+$; $R_f$=0.6 (dichloromethane:methanol/6:4).

Example 14

$N^4$-(tert-Butyloxycarbonyl)-$N^1$-methoxycarbonylmethylcytosine $N^4$-(tert-Butyloxycarbonyl)cytosine (1.6 g) is suspended in dry DMF (30 ml), sodium hydride (0.19 g) is added in portions, and the mixture is stirred for 1.5 hours at room temperature until the evolution of hydrogen has ceased. Methyl bromoacetate (0.84 ml) is subsequently added dropwise at room temperature using a syringe. stirring is continued for 5 hours at room temperature, and the mixture is then treated with methanol (1 ml). The solvent is stripped off in vacuo, and the residue which remains is purified by column chromatography on silica gel using dichloromethane as the eluent. The product-containing fractions are combined and concentrated in vacuo.

Yield: 1.1 g; MS(DCI): 284 (M+H)$^+$; $R_f$=0.5 (dichloromethane:methanol/95:5).

Example 15

$N^4$-(tert-Butyloxycarbonyl)-$N^1$-carboxymethylcytosine $N^4$-(tert-Butyloxycarbonyl)-$N^1$-methoxycarbonylmethylcytosine (4.2 g) is suspended in water (30 ml) and 2N aqueous sodium hydroxide solution is added dropwise at 0° C. while the pH is checked (pH 12) until the methyl ester is hydrolyzed. The course of the reaction is monitored by means of TLC. The pH of the reaction solution is then brought to 3 using acetic acid, and the solvent is distilled off in vacuo. The crude product is purified by column chromatography on silica gel using dichloromethane:methanol:triethylamine/8:1:1 as the eluent. The product-containing fractions are combined and concentrated in vacuo.

Yield: 3.5 g; M.p.: 95–98° C., decomposition; MS(FAB/NBA): 270.2 (M+H)$^+$; $R_f$=0.35 (dichloromethane:methanol:triethylamine/8:1:1).

Example 16

$N^6$-(4-Methoxybenzoyl)adenine

Adenine (13.5 g) is suspended in dry pyridine (250 ml). 4-Methoxybenzoyl chloride (17.06 g) is then added dropwise using a syringe. The mixture is stirred for 3 hours at 100° C. and allowed to stand overnight at room temperature. The reaction solution is then treated with methanol, and the solvent is subsequently distilled off in vacuo. The residue is coevaporated two more times using a small amount of toluene and then stirred with hot isopropanol. The mixture is allowed to cool slowly, and the product which has precipitated is filtered off with suction and dried in vacuo.

Yield: 22.2 g; M.p.: 212–214° C.; MS(ES$^+$): 270 (M+H)$^+$; $R_f$=0.67 (dichloromethane:isopropanol/8:2).

Example 17

N$^6$-(4-Methoxybenzoyl)-N$^9$-methyloxycarbonylmethyladenine

N$^6$-(4-Methoxybenzoyl)adenine (8.01 g) is suspended in dry DMF (150 ml), sodium hydride (0.75 g) is added in portions, and the mixture is stirred at room temperature for 0.5 hours until the evolution of hydrogen has ceased. Methyl bromoacetate (2.85 ml) is subsequently added dropwise at room temperature using a syringe. stirring is continued for 2 hours at room temperature, and the mixture is then treated with a small amount of carbon dioxide in methanol. The solvent is stripped off in vacuo, and the residue which remains is treated with dichloromethane/water and then filtered. The filter residue is also washed with a small amount of water and then dried in vacuo.

Yield: 4.03 g; MS(ES$^+$): 342 (M+H)$^+$; $R_f$=0.76 (ethyl acetate:methanol/8:2).

Example 18

N$^6$-(4-Methoxybenzoyl)-N$^9$-carboxymethyladenine

N$^6$-(4-Methoxybenzoyl)-N$^9$-methyloxycarbonylmethyladenine (1.71 g) is suspended in water (40 ml), and 2N aqueous sodium hydroxide solution is added dropwise at 0° C. while the pH is checked (pH 11.2) until the methyl ester is hydrolyzed. The course of the reaction is monitored by means of TLC. The reaction solution is then filtered, and the pH of the filtrate is brought to 3 using 2M potassium hydrogen sulfate solution, during which process the product precipitates. The precipitate is filtered off, washed with a small amount of cold water and dried in vacuo.

Yield: 1.52 g; M.p.: 222–223° C., decomposition; MS(ES$^+$): 328 (M+H)$^+$; $R_f$=0.2 (n-butanol/acetic acid/water 3:1:1).

Example 19

N$^2$-(Isobutanoyl)guanine

Guanine (3.02 g) is suspended in dry DMF (40 ml), and triethylamine (1.45 ml) is added. Isobutyryl chloride (2.12 g) is then added dropwise using a syringe. The mixture is stirred for 3 hours at 100° C., the reaction solution is then treated with methanol, and the solvent is subsequently distilled off in vacuo. The residue is stirred with hot isopropanol, and the product which has precipitated is filtered off with suction and dried in vacuo.

Yield: 2.67 g; $R_f$=0.45 (n-butanol/acetic acid/water 3:1:1).

Example 20

N$^2$-(Isobutanoyl)-N$^9$-methyloxycarbonylmethylguanine

N$^2$-(Isobutanoyl)guanine (4.42 g) is suspended in dry DMF (50 ml), sodium hydride (0.5 g) is added in portions, and the mixture is stirred for 1 hour at room temperature until the evolution of hydrogen has ceased. Methyl bromoacetate (1.9 ml) is subsequently added dropwise at room temperature using a syringe. stirring is continued for 1 hour at room temperature and the mixture is then treated with a small amount of carbon dioxide in methanol. The solvent is stripped of f in vacuo, and the residue which remains is purified by means of column chromatography on silica gel using dichloromethane:methanol/95:5 as the eluent. The product-containing fractions are combined and concentrated in vacuo.

Yield: 2.35 g; MS(DCl): 294(M+H)$^+$; $R_f$=0.58 (dichloromethane:methanol/9:1).

Example 21

N$^2$-(Isobutanoyl)-N$^9$-carboxymethylguanine

N$^2$-(Isobutanoyl)-N$^9$-methyloxycarbonylmethylguanine (9.68 g) is suspended in water (100 ml), and 2N aqueous sodium hydroxide solution is added dropwise at 0° C. while the pH is checked (pH 11) until the methyl ester is hydrolyzed. The course of the reaction is monitored by means of TLC. The reaction solution is then filtered, the pH of the filtrate is brought to 3 using 2M potassium hydrogen sulfate solution, and the mixture is extracted using ethyl acetate. The organic phase is discarded. The aqueous phase is concentrated in vacuo to a volume of approximately 20 ml and covered with a layer of ethyl acetate. The precipitate which separates out slowly is filtered off with suction and dried.

Yield: 1.35 g; MS(ES$^+$): 342 (M+H)$^+$; $R_f$=0.34 (n-Butanol:acetic acid:water/3:1:1).

Example 22

Preparation of N-(4-Methoxyphenyldiphenylmethylaminoethyl)glycine Methyl Ester

Mmt-Aeg-OMe 14.76 g of N-(aminoethyl)glycine methyl ester dihydrochloride (H-Aeg-OMe.2 HCl) are suspended in 300 ml of DMF and the suspension is treated with 30.2 ml of triethylamine, with stirring. The mixture is cooled to approximately 4° C., and 22.23 g of Mmt-Cl, dissolved in 100 ml of dichloromethane, are slowly added dropwise, with vigorous stirring. Stirring is continued for 2.5 hours at room temperature. Precipitated triethylamine hydrochloride is then filtered off, 10 ml of ethanol are added to the solution, and the filtrate is concentrated in vacuo. The residue is then chromatographed on silica gel using a mixture of diethyl ether/petroleum ether/triethylamine 200:100:3. The product-containing fractions are combined and evaporated to dryness in vacuo.

Yield: 18.82 g of oil which crystallizes slowly upon standing. $R_f$=0.16 (diethyl ether/petroleum ether 2:1 together with 1% of triethylamine); MS(FAB/MeOH/NBA/LiCl): 411.2 (M+Li)$^+$.

Example 23

Synthesis Protocol for the Preparation of N-((4-Methoxyphenyl)diphenylmethylamino)ethyl-N-((1-thyminyl)acetyl)glycine (Mmt-Aeg(T)-OH)

1.21 g (3 mmol) of Mmt-Aeg-OMe are dissolved in 20 ml of THF, and 0.24 ml of chloroacetyl chloride, dissolved in 10 ml of THF, and 0.42 ml of triethylamine, dissolved in 10 ml of THF, are simultaneously slowly added dropwise with cooling and vigorous stirring. The mixture is then allowed to afterreact for 30 minutes, triethylamine hydrochloride which has precipitated is filtered off with suction, and the solution is treated with 30 ml of dry DMF. The THF is subsequently stripped off in vacuo on a rotary evaporator, and 0.756 g (6 mmol) of thymine and 1.66 g (12 mmol) of finely pulverulent potassium carbonate are added in succession to the solution of Mmt-Aeg(chloroacetyl)-OMe in DMF. This mixture is stirred for 48 hours at room temperature, and undissolved matter is then filtered off with suction. The solvent is stripped off, and the residue is partitioned between water and ethyl acetate. After the solvent has been stripped off, the crude product which remains in the ethyl acetate phase is hydrolyzed in a mixture of dioxane/methanol/water by adding 35 ml of 0.2N NaOH. The residue which is obtained after the solvent has been stripped off is then subjected to chromatographic purification on silica gel using dichloromethane/MeOH/triethylamine (100/10/1). The product-containing fractions are combined and concentrated. 0.81 g of a colorless foam remains.

$R_f$=0.29 (dichloromethane/methanol/triethylamine 100:10:1); MS(ES$^-$): 1112.0 (2M–H)$^-$, 555.3 (M–H)$^-$.

Example 24

N-((4-Methoxyphenyl)diphenylmethylamino)ethyl-N-((1-thyminyl)acetyl)glycine Methyl Ester (Mmt-Aeg(T)-OMe)

1.00 g (2.48 mmol) of N-((4-Methoxyphenyl)diphenylmethyl)aminoethylglycine methyl ester is dissolved in 5 ml of DMF. 0.404 g (2.48 mmol) of 3,4-dihydro-3-hydroxy-4-oxo-1,2,3-benzotriazine and 0.632 ml (4.96 mmol) of 4-ethylmorpholine are added to this solution. A solution of 0.456 g (2.48 mmol) of N-1-carboxymethylthymine in 5 ml of DMF is then added dropwise, followed by 0.46 ml (3.0 mmol) of N,N'-diisopropylcarbodiimide. The reaction mixture is stirred for 20 hours at room temperature. The solvent is then removed in vacuo and the residue dissolved in ethyl acetate. This solution is washed twice with water and saturated potassium chloride solution. The organic phase is dried over sodium sulfate, filtered and then evaporated to dryness. The resulting crude product is purified chromatographically on silica gel which has been equilibrated with a mixture of dichloromethane/methanol/triethylamine (100/1/1), with a gradient of 1–5% of methanol in dichloromethane. The product-containing fractions are combined and concentrated in vacuo. 1.28 g of product are obtained as a colorless foam.

MS(FAB): 571.2 (M+H)$^+$; $R_f$=0.28 (CH$_2$Cl$_2$:MeOH/95:5).

Example 25

N-((4-Methoxyphenyl)diphenylmethylamino)ethyl-N-((1-thyminyl)acetyl)glycine (Mmt-Aeg(T))-OH The product of the above reaction is dissolved in a mixture of 10 ml of dioxane and 2 ml of water. The solution is cooled to 0° C., and 1N sodium hydroxide solution is added dropwise until a pH of 11 has been reached. After a reaction time of 2 hours, the reaction is complete, and the pH of the solution is brought to 5 by carefully adding 2N KHSO$_4$ solution. The solution is extracted three times using ethyl acetate, and the combined organic phases are dried over sodium sulfate and concentrated in vacuo. The resulting crude product is purified chromatographically on silica gel with a gradient of 5–10% of methanol and 1% of triethylamine in dichloromethane. The product-containing fractions are combined and concentrated in vacuo. Excess triethylamine which is still present is removed by coevaporation with pyridine and then toluene. 1.065 g of product are obtained as a colorless foam.

MS(ES$^-$): 1112.0 (1M—H)$^-$, 555.3 (M–H)$^-$; $R_f$=0.28 (CH$_2$Cl$_2$:MeOH/8:2).

Example 26

N-((4-Methoxyphenyl)diphenylmethylamino)ethyl-N-((1-(N$^4$-benzoyl)cytosyl)acetyl)glycine Methyl Ester (Mmt-Aeg(C$^{Bz}$)-OMe)

1.10 g N-((4-methoxyphenyl)diphenylmethyl) aminoethylglycine methyl ester (2.72 mmol) are dissolved in 5 ml of DMF and 0.444 g (2.72 mmol) of 3,4-dihydro-3-hydroxy-4-oxo-1,2,3-benzotriazine and 0.94 ml of 4-ethylmorpholine (5.45 mmol) are added. A suspension of 0.744 g (2.72 mmol) of N$^4$-benzoyl-N$^1$-carboxymethylcytosine in 20 ml of DMF is added, followed by 0.51 ml (3.27 mmol) of N,N'-diisopropylcarbodiimide. The reaction mixture is stirred for 20 hours at room temperature. The solvent is then stripped off in vacuo and the residue dissolved in ethyl acetate. This solution is washed twice using water and once using saturated sodium chloride solution. The organic phase is dried over sodium sulfate, filtered and concentrated in vacuo. The resulting crude product is purified chromatographically on silica gel which has been equilibrated with a mixture of dichloromethane/methanol/triethylamine (100/1/1) with a gradient of 1–2% of methanol in dichloromethane. The product-containing fractions are combined and concentrated in vacuo. 0.96 g of product is obtained as a yellowish white foam.

MS(ES$^-$) 658.6 (M–H)$^-$; $R_f$=0.37 (CH$_2$Cl$_2$:MeOH/95:5).

Example 27

N-((4-Methoxyphenyl)diphenylmethylamino)ethyl-N-((1-(N$^4$-benzoyl)cytosyl)acetyl)glycine (Mmt-Aeg(C$^{Bz}$))-OH 2.26 g (3.43 mmol) of N-((4-methoxyphenyl) diphenylmethylamino)ethyl-N-((1-(N$^4$-benzoyl)cytosyl) acetyl)glycine methyl ester are dissolved in 50 ml of dioxane. The solution is cooled to 0° C., and 34.4 ml of 1N sodium hydroxide solution are added dropwise. After 10 minutes, the pH is brought to 5 by dropwise addition of 1N KHSO$_4$, and salts which have precipitated are filtered off and washed with a small amount of dioxane. The combined filtrates are evaporated in vacuo, and the residue is coevaporated twice with methanol and dichloromethane. The resulting crude product is purified chromatographically on silica gel with a gradient of 5–10% of methanol and 1% of triethylamine in dichloromethane. The product-containing fractions are combined and concentrated in vacuo. Any excess triethylamine which is still present is removed by coevaporation with pyridine and then toluene. 1.306 g of product are obtained as a virtually white foam.

MS(ES$^-$) 644.3 (M–H)$^-$; $R_f$=0.68 (CH$_2$Cl$_2$:MeOH/8:2).

Example 28

N-((4-Methoxyphenyl)diphenylmethylamino)ethyl-N-((1-(N$^4$-(4-tert-butylbenzoyl)cytosyl)acetyl) glycine Methyl Ester (Mmt-Aeg(C$^{tBuBz}$)-OMe)

1.00 g (2.48 mmol) of N-((4-methoxyphenyl) diphenylmethyl)aminoethylglycine methyl ester is dissolved in 5 ml of DMF. 0.403 g (2.48 mmol) of 3,4-dihydro-3- hydroxy-4-oxo-1,2,3-benzotriazine and 0.63 ml (4.96 mmol) of 4-ethylmorpholine are added in succession to this solution. A suspension of 0.740 g (2.48 mmol) of $N^4$-(4-tert-butylbenzoyl)-$N^1$-carboxymethylcytosine in 5 ml of DMF is then added, followed by 0.47 ml of N,N'-diisopropylcarbodiimide. The mixture is stirred for 20 hours at room temperature and then evaporated to dryness in vacuo. The residue is dissolved in ethyl acetate, washed with water and saturated sodium chloride solution, dried over sodium sulfate, filtered and concentrated in vacuo. The crude product is purified using a silica gel column which has been equilibrated with a mixture of dichloromethane/ethyl acetate/triethylamine (50/50/1), using dichloromethane/ethyl acetate (1/1) as the eluent. The combined, product-containing fractions are concentrated in vacuo. The product is obtained as a yellowish white foam in a yield of 1.635 g.

MS(FAB/MeOH,NBA,LiCl): 722.5 (M+Li)$^+$; $R_f$=0.31 (CH$_2$Cl$_2$:ethyl acetate/1:1).

Example 29

N-((4-Methoxyphenyl)diphenylmethylamino)ethyl-N-((1-($N^4$-(4-tert-butylbenzoyl)cytosyl)acetyl) glycine (Mmt-Aeg(C$^{tBuBz}$)-OH)

1.63 g (2.28 mmol) of N-((4-methoxyphenyl)diphenylmethylamino)ethyl-N-((1-($N^4$-(4-tert-butylbenzoyl)cytosyl)acetyl)glycine methyl ester is dissolved in a mixture of 10 ml of dioxane and 1 ml of water and the mixture is treated dropwise with 4.56 ml of 1N NaOH at 0° C., with stirring. After 2 hours, the pH is brought to 5 by dropwise addition of 1N KHSO$_4$, and precipitated salts are filtered off and washed with a small amount of dioxane. The combined filtrates are evaporated in vacuo and the residue is coevaporated twice with methanol and dichloromethane. The resulting crude product is purified chromatographically on silica gel with a gradient of 2–10% of methanol and 1% of triethylamine in dichloromethane. The product-containing fractions are combined and concentrated in vacuo. Any excess triethylamine which is still present is removed by coevaporation with pyridine and subsequently toluene. 0.831 g of product is obtained as a virtually white foam.

MS(ES$^-$) 700.7 (M–H)$^-$; $R_f$=0.28 (CH$_2$Cl$_2$:MeOH/9:1), 0.63 (CH$_2$Cl$_2$:MeOH/7:3).

Example 30

N-((4-Methoxyphenyl)diphenylmethyloxy)ethyl-N-((1-thyminyl)acetyl)glycine (Mmt-Oeg(T)-OH)

0.5 g (1.28 mmol) of N-((4-methoxyphenyl)diphenylmethyloxy)ethylglycine is suspended in 10 ml of DMF, and 0.47 ml (1.92 mmol) of BSA is added dropwise. 0.7 ml (5.1 mmol) of triethylamine and 0.26 g (1.28 mmol) of chlorocarboxymethylthymine are then added in succession. The reaction mixture is stirred for 4 hours at room temperature, a further 65 mg (0.32 mmol) of chlorocarboxymethylthymine are then added, and the mixture is stirred for a further 16 hours. The solvent is then stripped off in vacuo and the crude product is purified on a silica gel column with a gradient of 5–15% of methanol and 1% of triethylamine in dichloromethane. The product-containing fractions are combined and concentrated in vacuo. The brownish oil obtained is dissolved in a small amount of dichloromethane and the product is precipitated by adding diethyl ether. The product is obtained as a virtually white powder.

Yield: 0.219 g; MS(ES$^-$) 556.3 (M–H)$^-$; $R_f$=0.54 (CH$_2$Cl$_2$:MeOH/8:2).

Example 31

N-((4-Methoxyphenyl)diphenylmethylamino)ethyl-N-((1-($N^4$-(4-methoxybenzoyl)cytosyl)acetyl) glycine Methyl Ester (Mmt-Aeg(C$^{MeOBz}$)-OMe)

N-((4-Methoxyphenyl)diphenylmethyl)aminoethylglycine methyl ester (4.00 g; 9.9 mmol) is dissolved in DMF (50 ml). To this solution there are added, in succession, 4-ethylmorpholine (3.44 ml), 3,4-dihydro-3-hydroxy-4-oxo-1,2,3-benzotriazine (1.62 g) $N^4$-(4-methoxybenzoyl)-$N^1$-carboxymethylcytosin (3.00 g; 9.9 mmol) and N,N'-diisopropylcarbodiimide (1.87 ml). The reaction mixture is stirred for 48 hours at room temperature. The solvent is then evaporated in vacuo and the residue taken up in ethyl acetate. This solution is extracted twice using water and once using saturated potassium chloride solution. The organic phase is dried over sodium sulfate, filtered and concentrated in vacuo. Purification is effected by means of column chromatography on silica gel which has previously been equilibrated with dichloromethane containing 1% of triethyl amine. Elution is effected with a gradient of 0–2% of methanol in dichloromethane containing 1% of triethylamine. The product-containing fractions are combined and concentrated in vacuo to a small volume. The dicyclohexylurea which precipitates during this process is filtered off, and the filtrate is evaporated in vacuo. The compound desired is obtained as a pale yellow foam.

Yield: 6.72 g; MS(FAB/MeOH,NBA,LiCl): 696.3 (M+Li)$^+$; $R_f$=0.59 (dichlormethane:methanol/9:1).

Example 32

N-((4-Methoxyphenyl)diphenylmethylamino)ethyl-N-((1-($N^4$-(4-methoxybenzoyl)cytosyl)acetyl) glycine (Mmt-Aeg(C$^{MeOBz}$)-OH)

N-((4-Methoxyphenyl)diphenylmethyl)aminoethyl-N-((1-($N^4$-(4-methoxybenzoyl))cytosyl)acetyl)glycine methyl ester (6.60 g; 9.6 mmol) is dissolved in a mixture of dioxane (50 ml) and water (50 ml), and the mixture is treated dropwise at 0° C. with 1M aqueous sodium hydroxide solution (15 ml) in two portions. After a reaction time of 2 hours, the solution is rendered neutral by adding ion exchanger (Dowex AG 50WX4, pyridinium form). The ion exchanger is filtered off and washed with aqueous dioxane and methanol. The combined filtrates are evaporated to dryness in vacuo and purified by column chromatography on silica gel by elution using 10% of methanol in dichloromethane (with 1% of triethylamine). The product is obtained as a yellowish white foam. A colorless powder is obtained after recrystallization from ethyl acetate.

Yield: 4.00 g; MS(ES$^-$): 674.1 (M–H)$^-$; $R_f$=0.39 (dichloromethane:methanol/9:1).

Example 33

N-((4-Methoxyphenyl)diphenylmethylamino)ethyl-N-(9-($N^2$-(isobutanoyl)guanosyl)acetyl)glycine Methyl Ester (Mmt-Aeg(G$^{iBu}$)-OMe)

N-((4-Methoxyphenyl)diphenylmethyl) aminoethylglycine methyl ester (1.45 g; 3.59 mmol) is dissolved in DMF (7 ml). To this solution there are added, in succession, 4-ethylmorpholine (1.24 ml; 7.17 mmol), 3,4-dihydro-3-hydroxy-4-oxo-1,2,3-benzotriazin (0.585 g; 3.59 mmol), $N^2$-(isobutanoyl)-$N^9$-carboxymethylguanine (1.00 g; 3.59 mmol) and N,N'-diisopropylcarbodiimide (0.67 ml: 4.31 mmol). The reaction mixture is stirred for 48 hours at 4° C. The solvent is then evaporated in vacuo and the residue taken up in ethyl acetate. This solution is extracted twice using water and once using saturated potassium chloride solution and the organic phase is dried over sodium sulfate, filtered and concentrated in vacuo. The yellow foam which remains is dissolved in a small amount of ethyl acetate and cooled with ice to precipitate dicyclohexylurea which is still present. After filtration, the filtrate is concentrated in vacuo. Purification is effected by means of column chromatography on silica gel which has previously been equilibrated with dichloromethane:ethyl acetate 1/1 containing 1% of triethylamine. Elution is effected using dichloromethane:ethyl acetate 1/1. The product-containing fractions are combined and concentrated in vacuo. The compound desired is obtained as a pale yellow foam.

Yield: 1.181 g; MS(FAB/MeOH,NBA,LiCl): 678.3 (M+2 Li−H)$^+$; 672.3 (M+Li)$^+$; $R_f$=0.13 (dichloromethane:methanol/95:5).

Example 34

N-((4-Methoxyphenyl)diphenylmethylamino)ethyl-N-(9-($N^2$-(isobutanoyl)guanosyl)acetyl)glycine (Mmt-Aeg($G^{iBu}$)-OH)

N-((4-Methoxyphenyl)diphenylmethylamino)ethyl-N-(9-($N^2$-(isobutanoyl)guanosyl)acetyl)glycine methyl ester (1.15 g; 1.72 mmol) is dissolved in dioxane (10 ml), and the solution is treated dropwise with 1M aqueous sodium hydroxide solution (10.32 ml) in 5 portions at 0° C. over a period of 2.5 hours. After a further reaction time of 2 hours at room temperature, the pH of the solution is brought to 5 by dropwise addition of 2M aqueous potassium hydrogen sulfate solution. The salts which have precipitated are filtered off and washed with a small amount of dioxane. The combined filtrates are evaporated to dryness in vacuo, and the residue is coevaporated in each case twice with ethanol and with dichloromethane:methanol 1/1. Purification is effected by column chromatography on silica gel by elution using a gradient of 10–20% of methanol in dichloromethane (with 1% of triethylamine). The product is obtained as a white foam.

Yield: 1.229 g; MS(ES$^-$): 650.3 (M—H)$^-$; $R_f$=0.25 (dichloromethane:methanol/8:2).

Example 35

N-((4-Methoxyphenyl)diphenylmethylamino)ethyl-N-(9-($N^6$-(4-methoxybenzoyl)adenosyl)acetyl) glycine Methyl Ester (Mmt-Aeg($A^{MeOBz}$)-OMe)

N-((4-Methoxyphenyl)diphenylmethyl)aminoethylglycine methyl ester (1.24 g; 3.06 mmol) is dissolved in DMF (7 ml). To this solution there are added, in succession, 4-ethylmorpholine (1.06 ml; 6.12 mmol), 3,4-dihydro-3-hydroxy-4-oxo-1,2,3-benzotriazin (0.498 g; 3.06 mmol), $N^6$-(4-methoxybenzoyl)-$N^9$-carboxymethyladenine (1.00 g; 3.06 mmol) and N,N'-diisopropylcarbodiimide (0.58 ml; 3.67 mmol). The reaction mixture is stirred for 48 hours at 4° C. The solvent is then evaporated in vacuo and the residue taken up in ethyl acetate. This solution is extracted twice using water and once using saturated potassium chloride solution. The organic phase is dried over sodium sulfate, filtered and concentrated in vacuo. The yellow foam which remains is dissolved in a small amount of ethyl acetate and cooled with ice to precipitate dicyclohexylurea which is still present. The dicyclohexylurea is filtered off and the filtrate concentrated in vacuo. Purification is effected by means of column chromatography on silica gel which has previously been equilibrated with dichloromethane:ethyl acetate 1/1 containing 1% of triethylamine. Elution is effected using dichloromethane:ethyl acetate 1/1. The product-containing fractions are combined and concentrated in vacuo. The desired compound is obtained as a pale yellow foam.

Yield: 1.752 g; MS(FAB/MeOH,NBA,LiCl): 720.3 (M+Li)$^+$; $R_f$=0.21 (dichloromethane:methanol/95:5).

Example 36

N-((4-Methoxyphenyl)diphenylmethylamino)ethyl-N-(9-($N^6$-(4-methoxybenzoyl)adenosyl)acetyl) glycine (Mmt-Aeg($A^{MeOBz}$)-OH)

N-((4-Methoxyphenyl)diphenylmethylamino)ethyl-N-(9-($N^6$-(4-methoxybenzoyl)adenosyl)acetyl)glycine methyl ester (1.70 g; 2.38 mmol) is dissolved in dioxane (10 ml) and the solution is treated dropwise with 1M aqueous sodium hydroxide solution (10.32 ml) in 5 portions at 0° C. over a period of 2.5 hours. After a further reaction time of 2 hours at room temperature, the pH of the solution is brought to 5 by dropwise addition of 2M aqueous potassium hydrogen sulfate solution. The salts which have precipitated are filtered off and washed with a small amount of dioxane. The combined filtrates are evaporated to dryness in vacuo and the residue is coevaporated in each case twice with ethanol and dichloromethane:methanol 1/1. Purification is effected by column chromatography on silica gel by elution using a gradient of 10–20% of methanol in dichloromethane (with 1% of triethylamine). the product is obtained as a white foam.

Yield: 1.619 g; MS(ES$^-$): 698.3 (M−H)$^-$; $R_f$=0.10 (dichloromethane:methanol/8:2).

Example 37

Thyminylacetic Acid (Preparation process as described by L. Kosynkina, W. Wang and T. Chyau Liang, Tetrahedron Lett. 1994, 5173–5176)

37.8 g of thymine are dissolved in a solution of 64.5 g of potassium hydroxide in 200 ml of water. A solution of 62.5 g of bromoacetic acid in 100 ml of water is then added dropwise at 40° C. in the course of 70 minutes, with vigorous stirring. Stirring is continued for 1 hour at 40° C., the solution is allowed to cool to 20° C., and the pH is brought to 5.5 by adding concentrated hydrochloric acid. The mixture is allowed to stand for 1.5 hours at 0° C., the unreacted thymine which has precipitated is filtered off with suction, and the pH of the filtrate is then brought to 2.0 using concentrated hydrochloric acid, during which process the product precipitates. The product is allowed to stand for a further hour at 0° C., and the precipitate is then filtered off with suction and dried in a desiccator.

Yield: 52.19 g; $R_f$=0.23 (ethyl acetate/methanol/glacial acetic acid 75:20:5); MS(DCI): 185 (M+H)$^+$;

Example 38

Methyl Thyminylacetate 31.5 g of thymine are suspended in 800 ml of dry DMF, and 69.4 g of finely pulverulent potassium carbonate are added. The mixture is shaken for 3 hours at room temperature, and 23.1 ml of methyl bromoacetate are then added. The mixture is shaken overnight under argon, the precipitate is then filtered off and washed with DMF, and the filtrate is concentrated in vacuo on a rotary evaporator. The residue is triturated thoroughly in a mortar in a mixture of 240 ml of water and 19 ml of 2N HCl, and the precipitate is then filtered off with suction and washed with water. The resulting crude product, which is still moist with water, is recrystallized from 450 ml of methanol.

Yield: 25.5 g; $R_f$=0.78 (ethyl acetate/methanol/glacial acetic acid 80:10:5); MS(DCI): 199.1 $(M+H)^+$.

Example 39

N-((4-Methoxyphenyl)diphenylmethylamino)ethyl-N-((1-thyminyl)acetyl)glycine Methyl Ester
Mmt-Aeg(T)-OMe 19.84 g of Mmt-Aeg-OMe are dissolved in 450 ml of THF, and then 6.82 ml of triethylamine are first added with cooling and vigorous stirring, followed by 3.92 ml of chloroacetyl chloride, slowly added dropwise, dissolved in 60 ml of THF. After approximately 2/3 of the chloroacetyl chloride solution have been added dropwise, a further 3.41 ml of triethylamine are added. After the addition of chloroacetyl chloride has ended, the mixture is allowed to after-react for one hour, precipitated triethylamine hydrochloride is filtered off with suction, and the solution is treated with 400 ml of dry DMF. The THF is subsequently stripped off in vacuo on a rotary evaporator, and this solution of Mmt-Aeg(chloroacetyl)OMe in DMF is added to a mixture of 12.36 g of thymine and 27.16 g of finely pulverulent potassium carbonate in 200 ml of dry DMF, which has already pre-reacted overnight. This mixture is stirred for a further 16 hours at room temperature, and undissolved matter is then filtered off with suction. The filtrate is concentrated in vacuo on a rotary evaporator, and the residue is partitioned between water and ethyl acetate. The organic phase is dried over sodium sulfate, the dessicant is filtered off in vacuo and the filtrate is then concentrated on a rotary evaporator to a volume of approximately 80 ml. This solution is then stirred into a mixture of 600 ml of petroleum ether and 200 ml of diethyl ether, during which process the product precipitates.

Yield: 25 g; $R_f$=0.34 (dichloromethane/methanol/triethylamine 100:5:1).

Example 40

N-((4-Methoxyphenyl)diphenylmethylamino)ethyl-N-((1-thyminyl)acetyl)glycine
Mmt-Aeg(T)-OH 5.7 g of Mmt-Aeg(T)-OMe are suspended in 25 ml of water, and the suspension is treated in succession with 13.9 ml of triethylamine and 12.5 ml of dioxane. The resulting clear solution is allowed to stand for 72 hours at room temperature, and the solvent is then distilled off in vacuo on a rotary evaporator. This process is followed by three distillations using small amounts of toluene. The residue is taken up in a mixture of in each case 20 ml of dioxane and ethyl acetate, a small amount of undissolved matter is filtered off, and the filtrate is stirred into 500 ml of ether containing 1% of triethylamine. The product which has precipitated is filtered off with suction and dried in a desiccator.

Yield: 4.1 g; $R_f$=0.28 (dichloromethane/methanol/triethylamine 100:10:1).

Example 41

N-((4-Methoxyphenyl)diphenylmethylamino)ethyl-N-((1-thyminyl)acetyl)glycine
Mmt-Aeg(T)-OH 5.7 g Mmt-Aeg(T)-OMe are dissolved in a mixture of 80 ml of water, 20 ml of methanol and 13.9 ml of triethylamine. The resulting clear solution is stirred for 24 hours at room temperature, and the solvent is then distilled off in vacuo on a rotary evaporator. This is followed by three distillations using small amounts of toluene. The residue is taken up in a mixture of in each case 20 ml of dioxane and ethyl acetate, a small amount of undissolved matter is filtered off, and the filtrate is stirred into 500 ml of ether containing 1% of triethylamine. The product which has precipitated is filtered off with suction and dried in a desiccator.

Yield: 4.8 g; $R_f$=0.28 (dichloromethane/methanol/triethylamine 100:10:1).

Example 42

N-((2-Hydroxy)ethyl-N-((1-thyminyl)acetyl)glycine
H-Oeg(T)-OH 2.76 g of thyminylacetic acid are dissolved in 15 ml of dry DMF, and 4.92 g of TOTU and 2.08 ml of triethylamine are added. Stirring of the mixture is continued for 30 minutes at room temperature, and the mixture is then slowly added dropwise to a solution composed of 3.57 g of (2-hydroxyethyl)glycine, 10 ml of water, 10 ml of DMF and 4.16 ml of triethylamine. stirring is continued for 1 hour at room temperature, and 20 ml of acetonitrile are then added, during which process the excess hydroxyethylglycine precipitates. The precipitate is filtered off with suction, and the filtrate is concentrated in vacuo on a rotary evaporator. The residue is taken up in water, the pH is brought to 1.5 using 1N hydrochloric acid, and the mixture is extracted using ethyl acetate. The pH of the aqueous phase is brought to 5 using saturated sodium hydrogen carbonate solution and it is concentrated on a rotary evaporator. The residue is treated with 250 ml of ethanol, and the sodium chloride which has precipitated in this process is filtered off with suction. The filtrate is concentrated, and the crude product is purified chromatographically on silica gel using dichloromethane/methanol/ethyl acetate 10:2:1 with an addition of 1% of triethylamine. The product-containing fractions are combined and concentrated in vacuo on a rotary evaporator.

Yield: 2.39 g; $R_f$=0.17 (dichloromethane/methanol/ethyl acetate 10:2:1+1% of triethylamine); MS(DCl): 286 $(M+H)^+$.

Example 43

N-(2-(di-(4-Methoxyphenyl)phenyl)methyloxy)ethyl-N-((1-thyminyl)acetyl)glycine
Dmt-Oeg(T)-OH 1.76 g of H-Oeg(T)-OH are dissolved in 30 ml of DMF, 3.41 ml of triethylamine are added, and a solution of 4.16 g of Dmt-Cl in 30 ml of dichloromethane is added dropwise at 0° C. in the course of 20 minutes. Stirring is continued for 3 hours at room temperature, the triethylamine hydrochloride which has precipitated is then filtered off, and the filtrate is concentrated in vacuo on a rotary evaporator. The crude product is purified on silica gel using dichloromethane/methanol/ethyl acetate 10:2:1 with an addition of 1% of triethylamine. The product-containing fractions are combined and concentrated in vacuo on a rotary evaporator.

Yield: 3.2 g; $R_f$=0.29 (dichloromethane/methanol/ethyl acetate 10:2:1+1% triethylamine); MS($ES^+$+LiCl): 594.3 (M+Li)+, 600.4 $(M+2Li-H)^+$.

Example 44

Preparation of N-(2-(di-(4-Methoxyphenyl)phenyl)methylthio)ethyl-N-((1-thyminyl)acetyl)glycine Dmt-Teg(T)-OH

Example 44a

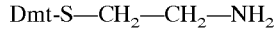
Dmt-S—CH$_2$—CH$_2$—NH$_2$ 10.17 g of Dmt-Cl are dissolved in 100 ml of acetic acid, and 4.43 g of 2-mercaptoethylamine hydrochloride, dissolved in 70 ml of water, are added. Stirring is continued for 2 hours at room temperature, and the mixture is then concentrated on a rotary evaporator to a volume of approximately 50 ml. 200 ml of water are then added, and the pH of the solution is brought to 10 using 2N NaOH, during which process the substance precipitates. The mixture is extracted 3 times using 100 ml of ethyl acetate in each case, and the combined organic phases are washed with saturated NaCl solution and dried over sodium sulfate. The desiccant is filtered off, and the filtrate is concentrated in vacuo on a rotary evaporator. The resulting crude product is employed in the subsequent reaction without further purification.

Yield: 14.75 g.

Example 44b

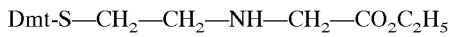
Dmt-S—CH$_2$—CH$_2$—NH—CH$_2$—CO$_2$C$_2$H$_5$ 12.56 g of Dmt-S—CH$_2$—CH$_2$—NH$_2$ (crude product of 44 a) are dissolved in 100 ml of dry DMF, and the solution is treated in succession with stirring at room temperature with 4.6 ml of triethylamine and 3.66 ml of ethyl bromoacetate. Stirring is continued for 3 hours, a small amount of precipitate is filtered off, and the filtrate is concentrated in vacuo on a rotary evaporator. The residue is taken up in 150 ml of ethyl acetate and washed 4 times using 40 ml of water in each case, the organic phase is dried over sodium sulfate, the desiccant is filtered off, and the filtrate is then concentrated in vacuo on a rotary evaporator. The resulting crude product is employed in the subsequent reaction without further purification.

Yield: 12.92 g.

Example 44c

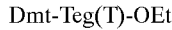
Dmt-Teg(T)-OEt 5.95 g of Dmt-S—CH$_2$—CH$_2$—NH—CH$_2$—CO$_2$C$_2$H$_5$ are dissolved in 50 ml of dry DMF and treated in succession with 2.36 g of thyminylacetic acid, 4.45 ml of triethylamine and 4.2 g of TOTU. The mixture is stirred for 2 hours at room temperature and allowed to stand overnight. The reaction mixture is then concentrated in vacuo on a rotary evaporator, the residue is taken up in 150 ml of ethyl acetate, the mixture is washed 5 times using in each case 10 ml of saturated sodium hydrogen carbonate solution and twice using 10 ml of water, and the organic phase is dried over sodium sulfate. The desiccant is filtered off, and the filtrate is concentrated in vacuo on a rotary evaporator. An oily crude product is obtained which is employed in the subsequent reaction without further purification.

Yield: 8.06 g.

Example 44d

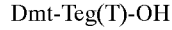
Dmt-Teg(T)-OH 8.06 g of Dmt-Teg(T)-OEt are dissolved in a mixture of 80 ml of dioxane and 40 ml of water and hydrolyzed by adding a total of 13 ml of 2N sodium hydroxide solution in portions. The solution is then concentrated in vacuo on a rotary evaporator to approximately 50 ml and extracted four times using in each case 50 ml of ethyl acetate. The pH of the aqueous phase is then brought to 5 using 2N hydrochloric acid and extracted four times using 50 ml of ethyl acetate. The combined organic phases are washed twice using in each case 30 ml of water and dried over sodium sulfate. The desiccant is filtered off, and the filtrate is concentrated in vacuo on a rotary evaporator to a volume of approximately 30 ml. A small amount of triethylamine is added, and the solution is stirred into 300 ml of diisopropyl ether, during which process the product precipitates. To purify the product further, it is chromatographed on silica gel using a step gradient of 0–5% of methanol in dichloromethane (1% of triethylamine in all eluents). The product-containing fractions are combined and concentrated in vacuo on a rotary evaporator.

Yield: 2.38 g; R$_f$=0.38 (dichloromethane/methanol/triethylamine 100:10:1); MS(FAB/NBA+LiCl): 610.2 (M+Li)$^+$, 616.2 (M+2Li—H)$^+$.

Example 45

2-N-Acetyl-4-O-diphenylcarbamoyl-9-methoxycarbonylmethylguanine 15.52 g of 2—N-acetyl-4-O-diphenylcarbamoylguanine (prepared as described by R. Zou and M. J. Robins, Can J. Chem. 65, 1436–1437, 1987) are suspended in 200 ml of dry DMF, 13.6 ml of diisopropylethylamine are added, and the mixture is then heated briefly until a clear solution has formed. 4.04 ml of methyl bromoacetate are then added and the solution is stirred overnight. The solvent is subsequently removed in vacuo on a rotary evaporator and the residue dissolved in 200 ml of methanol. This solution is stirred into 600 ml of water with vigorous stirring, during which process the product precipitates. The resulting crude product is filtered off with suction, washed with water and redissolved in methanol, the solution is concentrated to dryness, and the product is triturated with ethyl acetate. The resulting product is filtered off with suction, washed with ethyl acetate and ether and then dried in vacuo. More product is obtained from the mother liquor after concentration and retrituration with ethyl acetate.

Yield: 13.2 g; MS(ES$^+$): 461.3 (M+H)$^+$; R$_f$=0.79 (2-butanone/pyridine/water/acetic acid 70:15:15:2).

Example 46

2-N-Acetyl-4-O-diphenylcarbamoyl-9-carboxymethylguanine 7.54 g of 2—N-acetyl-4-O-diphenylcarbamoyl-9-methoxycarbonylmethylguanine are dissolved in a mixture of 20 ml of methanol, 80 ml of dioxane and 40 ml of water and hydrolyzed with a total of 18 ml of 1N NaOH at a pH of 13. The pH of the solution is then brought to 6 by adding 1N hydrochloric acid and the mixture is evaporated in vacuo on a rotary evaporator to a volume of approximately 50 ml. After 400 ml of water have been added, the pH is brought to 3 using 1N hydrochloric acid, during which process the product precipitates. The product is filtered off with suction, washed with water and dried in a desiccator.

Yield: 5.92 g; MS(ES$^+$): 447.2 (M+H)$^+$; R$_f$=0.48 (2-butanone/pyridine/water/acetic acid 70:15:15:2).

Example 47

N-((4-Methoxyphenyl)diphenylmethylamino)ethyl-
N-((9-($N^2$-acetyl-$O^4$-diphenylcarbamoyl)guanosyl)
acetyl)glycine Methyl Ester Mmt-Aeg($G^{2-Ac,4-Dpc}$)-OMe 3.57 g of 2-N-acetyl-4-O-diphenylcarbamoyl-9-carboxymethylguanine are dissolved in 120 ml of dry DMF, and 3.23 g of Mmt-Aeg-OMe, 2.62 g of TOTU and, in portions, 4.08 ml of diisopropylethylamine are added in succession. The mixture is stirred for 4 hours at room temperature and left to stand overnight. The solvent is then distilled off in vacuo on a rotary evaporator and the residue is partitioned between 160 ml ethyl acetate and 20 ml of water. The organic phase is extracted three times using in each case 20 ml of water and dried over sodium sulfate, the desiccant is filtered off, and the filtrate is concentrated. The residue which remains is triturated repeatedly with diethyl ether, and the product which has then separated out as a precipitate is filtered off with suction and dried in a desiccator.

Yield: 5.53 g; $R_f$=0.63 (dichloromethane/methanol/triethylamine 100:5:1).

Example 48

N-((4-Methodyphenyl)diphenylmethylamino)ethyl-
N-((9-($N^2$-acetyl-$O^4$-diphenylcarbamoyl)guanosyl)
acetyl)glycine Mmt-Aeg($G^{2-Ac,4-Dpc}$)-OH 4.99 g Mmt-Aeg($G^{2-Ac,4-Dpc}$)-OMe are dissolved in a mixture of 50 ml of dioxane and 10 ml of water and hydrolyzed by adding a total of 15 ml of 0.5N NaOH in portions. The pH of the solution is then brought to 9 using 0.5N HCl and the solvent is stripped off in vacuo on a rotary evaporator. This is followed by one more distillation with a small amount of toluene, and the residue is then dissolved in 30 ml of methanol. This solution is stirred into 300 ml of diethyl ether (which has been treated with 1% of triethylamine), during which process the product precipitates. The precipitate, which is still somewhat tacky, is triturated with diethyl ether, filtered off with suction and dried in a desiccator. It is purified further by means of chromatography on silica gel using a 10 step gradient (4–16%) of methanol/ethyl acetate (1:1) in dichloromethane, with 1% of triethylamine in all solvents. The product-containing fractions are combined and concentrated in vacuo on a rotary evaporator.

Yield: 2.68 g; $R_f$=0.18 (dichloromethane/methanol/triethylamine 100:7.5:1); MS($ES^+$+LiCl): 819.4 $(M+H)^+$, 825.3 $(M+Li)^+$.

Example 49

1-Acetyl-2,4-dihydroxy-5-methylpyrimidine
1-Acetylthymine 75 g of thymine are suspended in 375 ml of acetic anhydride and refluxed for 45 minutes. The mixture is then cooled to 0° C., during which process the product precipitates. The precipitate is filtered off with suction and stirred with 375 ml of ethyl acetate. The precipitate is filtered off with suction, washed with a small amount of diethyl ether and dried.

Yield: 89.1 g; Melting point: 187–189° C.; $R_f$=0.67 (dichloromethane/methanol 95:5).

Example 50

3-Benzyloxymethyl-2,4-dihydroxy-5-methylpyrimidine

3-Benzyloxymethylthymine 52.0 g of 1-acetyl-2,4-dihydroxy-5-methylpyrimidine are suspended in 300 ml of DMF, 47.5 ml of triethylamine are added, and the mixture is cooled to 0° C. 100 ml of benzyl chloromethyl ether in 50 ml of DMF are slowly added dropwise to the thoroughly stirred mixture at this temperature. Stirring is continued for 1 hour and the mixture is left to stand overnight at room temperature. The reaction mixture is then concentrated in vacuo on a rotary evaporator, taken up in 450 ml of methanol and 300 ml of a 40% aqueous solution of methylamine and refluxed for 1.5 hours. The solution is then concentrated and stirred with 10.8 g of sodium hydrogen carbonate in 600 ml of water. The product which has precipitated is filtered off with suction, washed with water and ethanol and recrystallized from ethanol.

Yield: 46.66 g; Melting point: 119–120° C.; $R_f$=0.38 (dichloromethane/methanol 95:5).

Example 51

Ethyl 3-Benzyloxymethyl-2,4-dihydroxy-5-methylpyrimidineacetate

3-Benzyloxymethyl-1-ethoxycarbonylmethylthymine 4.97 g of sodium hydride are introduced into 150 ml of THF, 45.04 g of 3-benzyloxymethyl-2,4-dihydroxy-5-methylpyrimidine, dissolved in 550 ml of THF, are then added dropwise at 0° C. under an $N_2$ atmosphere, and 21.42 ml of ethyl bromoacetate in 700 ml of THF are subsequently added at this temperature. Thereinafter, stirring of the mixture is continued for 5 hours at room temperature, and water is subsequently added carefully. The organic phase is separated off, and the aqueous phase is reextracted four times using dichloromethane. The combined organic phases are dried over magnesium sulfate and concentrated, and the residue is stirred with heptane.

Yield: 54.2 g; $R_f$=0.15 (dichloromethane/methanol 95:5); MS(FAB, NBA): 319.1 $(M+H)^-$.

Example 52

Ethyl 2,4-Dihydroxy-5-methylpyrimidineacetate
Ethyl Thyminylacetate 25 g of ethyl 3-benzyloxymethyl-2,4-dihydroxy-5-methylpyrimidineacetate are dissolved in 1000 ml of dichloromethane, the mixture is cooled to −70° C., and 375 ml of a 1M solution of boron trichloride in dichloromethane is added dropwise at this temperature with vigorous stirring. The mixture is allowed to afterreact for 3 hours at this temperature, whereupon 320 ml of methanol are added dropwise at −70° to −60° C. After 1 hour, 197.05 ml of triethylamine are added and the mixture is allowed to come to room temperature. A small amount of water is then also added and the mixture is concentrated on a rotary evaporator. The residue is taken up in ethyl acetate and washed with water. The organic phase is dried over magnesium sulfate and then concentrated to dryness.

Yield: 12 g; $R_f$=0.45 (dichloromethane/methanol 9:1); MS(DCI): 199 $(M+H)^+$.

Example 53

2,4-Dihydroxy-5-methylpyrimidineacetic Acid
Thyminylacetic Acid 10 g of ethyl 2,4-dihydroxy-5-methylpyrimidineacetate are dissolved in 130 ml of dioxane/water (1:1), 60 ml of 1N LiOH are added and the mixture is then stirred overnight at room temperature. The mixture is then concentrated to a small volume, the aqueous phase is washed with ether, and the pH is then brought to 2.5. During this process, the product precipitates. It is filtered off with suction, 4.9 g being obtained. A further 1.5 g of product can be obtained from the mother liquor by extraction with pentanol and precipitation with heptane/ether.

Yield: 6.4 g; $R_f$=0.30 (dichloromethane/methanol 3:2); MS(DCI): 185 (M+H)$^+$.

Example 54

N-1-Chlorocarboxymethylthymine
Thyminylacetyl Chloride

Example 54a 2 g of 2,4-dihydroxy-5-methylpyriminidineacetic acid and 15 ml of thionyl chloride are stirred for 3 hours at 60° C., until-the evolution of gas has ceased. The excess thionyl chloride is then stripped off in vacuo on a rotary evaporator, and this is followed by three more distillations with small amounts of toluene. The resulting product is employed directly in the subsequent reaction.

Yield: 2.4 g; MS(DCI): 203 (M+H)$^+$;

Example 54b

N-1-Carboxymethylthymine (3.0 g; 16.3 mmol) is suspended in thionyl chloride (90 ml). The suspension is heated at 70° C. for 1.5 hours and then left to stand at room temperature for 16 hours. The excess thionyl chloride is removed in vacuo and the residue coevaporated three times using toluene. The product obtained is triturated twice using n-hexane and dried in vacuo. The compound is obtained as a pale orange powder.

Yield: 3.30 g; MS(DCI; dichloromethane): 203 (M+H)$^+$; $R_f$=0.10 (dichloromethane/methanol 7:3).

Example 55

Preparation of N-((4-Methoxyphenyl) diphenylmethylamino)ethyl-N-((1-imidazolyl)acetyl) glycine Methyl Ester

Mmt-Aeg(Im)-OMe 4.68 g of Mmt-Aeg-OMe are dissolved in 150 ml of THF, and 0.95 ml of chloroacetyl chloride dissolved in 15 ml of THF simultaneously with 3.3 ml of triethylamine dissolved in 10 ml of THF are slowly added dropwise with cooling and vigorous stirring. The mixture is then allowed to afterreact for 45 minutes, precipitated triethylamine hydrochloride is filtered off with suction, and the solution is treated with 150 ml of dry DMF. The THF is subsequently stripped off in vacuo on a rotary evaporator, and 1.62 g of imidazole and 6.55 g of finely pulverulent potassium carbonate are added in succession to the solution of Mmt-Aeg(chloroacetyl)-OMe in DMF. After 16 hours, undissolved salt is filtered off, and a further 1.62 g of imidazole and 6.55 g of finely pulverulent potassium carbonate are added to the filtrate. This mixture is stirred for a further 16 hours at room temperature and undissolved matter is then filtered off with suction. The filtrate is concentrated in vacuo on a rotary evaporator and the residue partitioned between water and ethyl acetate. The organic phase is dried over sodium sulfate and then evaporated after the desiccant has been filtered off. The residue is taken up in dichloromethane and precipitated by stirring into a mixture of diethyl ether/petroleum ether 4:1. After the solvent has been decanted off and the precipitate, still somewhat tacky, has been triturated with ether, the precipitate solidifies.

Yield: 3.96 g; $R_f$=0.39 (dichloromethane/methanol/triethylamine 100:5:1).

Example 56

Preparation of N-((4-Methoxyphenyl) diphenylmethylamino)ethyl-N-((1-imidazolyl)acetyl) glycine

Mmt-Aeg(Im)-OH 1.79 g of N-((4-methoxyphenyl)diphenylmethylamino) ethyl-N-((1-imidazolyl)acetyl)glycine methyl ester are dissolved in a mixture of 50 ml of dioxane and 25 ml of water and hydrolyzed by adding 5.25 ml of 1N NaOH. The pH of the solution is then brought to 8 using 1N HCl and the mixture is concentrated to dryness in vacuo on a rotary evaporator. The residue is subjected to two more distillations using small amounts of toluene and then purified chromatographically on silica gel using dichloromethane/methanol/ ethyl acetate 100:10:5 with 1% of triethylamine. The product-containing fractions are combined and concentrated to dryness in vacuo on a rotary evaporator.

Yield: 1.70 g; $R_f$=0.27 (dichloromethane/methanol/triethylamine 100:20:1); MS(ES$^+$): 499.3 (M+H)$^+$.

Further syntheses involving a chloroacetyl intermediate step are described hereinbelow:

Example 57

Preparation of the Solution of N-((4-Methoxyphenyl)diphenylmethylamino)ethyl-N-(chloroacetyl)glycine Methyl Ester in DMF

Mmt-Aeg(chloroacetyl)-OMe 34.85 g of Mmt-Aeg-OMe are dissolved in 900 ml of THF and then 6.9 ml of chloroacetyl chloride, dissolved in 110 ml of THF, and 24 ml of triethylamine, dissolved in 110 ml of THF, are simultaneously slowly added dropwise with cooling and vigorous stirring. The mixture is then allowed to afterreact for 1 hour, precipitated triethylamine hydrochloride is filtered off with suction, and the solution is treated with 600 ml of dry DMF. The THF is subsequently stripped off in vacuo on a rotary evaporator. The resulting solution of Mmt-Aeg(chloroacetyl)-OMe in DMF is divided.

Example 58

Preparation of N-((4-Methoxyphenyl) diphenylmethylamino)ethyl-N-((1-(4-nitro) imidazolyl)acetyl)glycine Methyl Ester

Mmt-Aeg(Im$^{4\text{-}Nitro}$)-OMe

To one half of the above-prepared solution of Mmt-Aeg-(chloroacetyl)-OMe in DMF there are added 9.75 g of finely pulverulent 4-nitroimidazole and 23.85 g of finely pulverulent potassium carbonate. This mixture is stirred for a further 16 hours at room temperature and undissolved matter is then filtered off with suction. The filtrate is concentrated in vacuo on a rotary evaporator and the residue is partitioned between water and ethyl acetate. The organic phase is washed three times using in each case 50 ml of water and dried over sodium sulfate, the desiccant is filtered off, and the filtrate is concentrated in vacuo on a rotary evaporator to a volume of approximately 60 ml. This solution is then stirred into a mixture of 400 ml of petroleum ether and 200 ml of diethyl ether, during which process the product precipitates. The product is filtered off with suction and dried in a desiccator.

Yield: 19.8 g; $R_f$=0.40 (dichloromethane/methanol/triethylamine MS(ES$^+$): 558.3 (M+H)$^+$.

Example 59

Preparation of N-((4-Methoxyphenyl) diphenylmethylamino)ethyl-N-((1-(4-nitro) imidazolyl)acetyl)glycine Mmt-Aeg(Im$^{4-Nitro}$)-OH 5.37 g of N-((4-methoxyphenyl)diphenylmethylamino) ethyl-N-((1-(4-nitro)imidazolyl)acetyl)glycine methyl ester are dissolved in a mixture of 20 ml of methanol, 80 ml of water and 13.9 ml of triethylamine. The clear solution is left to stand at room temperature for 48 hours. After this period, the starting material has undergone hydrolysis, and the solution is concentrated to dryness in vacuo on a rotary evaporator. The residue is subjected to two more distillations using small amounts of toluene. The residue is taken up in a mixture of in each case 20 ml of dioxane and ethyl acetate, a small amount of undissolved matter is filtered off, and the filtrate is stirred into 500 ml of ether containing 1% of triethylamine. The product which has precipitated is filtered off with suction, washed with a small amount of ether and dried in a desiccator.

Yield: 4.21 g; $R_f$=0.24 (dichloromethane/methanol/triethylamine 100:10:1); MS(ES$^+$): 543.2 (M$^+$).

Example 60

Preparation of N-((4-Methoxyphenyl) diphenylmethylamino)ethyl-N-((1-(1,2,4)-triazolyl) acetyl)glycine Methyl Ester Mmt-Aeg(Triaz)-OMe To the second half of the above-prepared solution of MMt-Aeg(chloroacetyl)-OMe in DMF there are added 5.96 g of finely pulverulent 1,2,4-triazole and 23.85 g of finely pulverulent potassium carbonate. This mixture is stirred for a further 16 hours at room temperature and undissolved matter is then filtered off with suction. The filtrate is concentrated in vacuo on a rotary evaporator, and the residue is partitioned between water and ethyl acetate. The organic phase is washed three times using in each case 50 ml of water and dried over sodium sulfate, the desiccant is filtered off, and the filtrate is then concentrated in vacuo on a rotary evaporator to a volume of approximately 60 ml. This solution is then stirred into a mixture of 400 ml of petroleum ether and 200 ml of diethyl ether, during which process the product precipitates. The product is filtered off with suction and dried in a desiccator.

Yield: 17.4 g; $R_f$=0.63 (dichloromethane/methanol/triethylamine 100:5:1).

Example 61

Preparation of N-((4-Methoxyphenyl) diphenylmethylamino)ethyl-N-((1-(1,2,3)-triazolyl) acetyl)glycine Mmt-Aeg(Triaz)-OH 5.13 g of N-((4-methoxyphenyl)diphenylmethylamino) ethyl-N-((1-(1,2,3)-triazolyl)acetyl)glycine methyl ester are dissolved in a mixture of 10 ml of dioxane, 10 ml of methanol, 80 ml of water and 13.9 ml of triethylamine. The clear solution is left to stand at room temperature for 48 hours. After this period, the starting material has undergone hydrolysis, and the solution is concentrated to dryness in vacuo on a rotary evaporator. The residue is subjected to two more distillations using small amounts of toluene. The residue is taken up in a mixture of in each case 20 ml of dioxane and ethyl acetate, a small amount of undissolved matter is filtered off, and the filtrate is stirred into 500 ml of ether containing 1% of triethylamine. The crude product which has precipitated (4.02 g) is purified chromatographically on silica gel using a step gradient (2–15%) of methanol/ethyl acetate (:1) in dichloromethane, with 1% of triethylamine in all solvents. The product-containing fractions are combined and concentrated to dryness in vacuo on a rotary evaporator.

Yield: 3.25 g; $R_f$=0.27 (dichloromethane/methanol/triethylamine 100:10:1); MS(ES$^+$): 500.2 (M+H)$^+$.

What is claimed is:

1. A process for the preparation of a compound of the formula (I) or a salt thereof

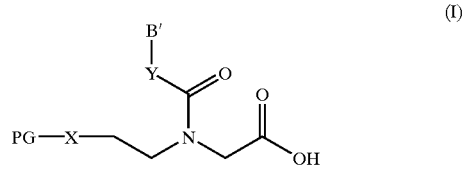

wherein

PG is a trityl type protective group which is labile to weak acids, and is selected from triphenylmethyl (Trt), (4-methoxyphenyl)diphenylmethyl (Mmt), (4-methylphenyl)-diphenylmethyl (Mtt), di-(4-methoxyphenyl)phenylmethyl (Dmt), and 9-(9-phenyl)xanthenyl(pixyl);

X is NH, O, or S;

Y is CH$_2$; and

B' is a base selected from adenine, cytosine, guanine, thymine, uracil, purine, 2,6-di-aminopurine, 7-deazaadenine, 7-deazaguanine, N$^4$N$^4$-ethanocytosine, N$^6$N$^6$-ethano-2,6-diaminopurine, 5-methylcytosine, 5-(C$_2$–C$_6$)alkynyluracil, 5-(C$_2$–C$_6$)alkynylcytosine, 5-fluorouracil and pseudoisocytosine, wherein any exocyclic amino or hydroxyl group is protected by a protective group, or B' is further selected from imidazole, triazole, and nitroimidazole;

which comprises reacting a compound of the formula (II)

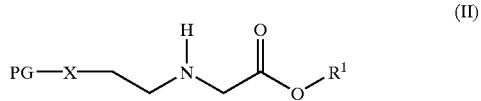

wherein PG and X are as defined above, and R$^1$ is hydrogen or an ester protective group, with a compound of the formula (III)

wherein B' and Y are as defined above, at 0–45° C. in a suitable solvent or mixtures of these solvents using a coupling reagent conventionally used in peptide chemistry, to give a compound of the formula (IV)

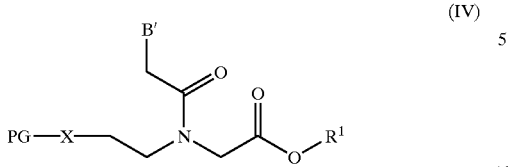
(IV)

wherein PG, X, B', and R¹ are as defined above, and subsequently converting this compound to a compound of the formula (I) by eliminating the ester protective group R¹ under weakly alkaline conditions using alkali metal hydroxide solution, or by tertiary amine compounds in water, or enzymatically with the aid of esterases or lipases at 0–50° C. in a suitable solvent or mixtures of these solvents, and wherein the resulting compound of the formula I may, optionally, be converted to a salt.

2. A process for the preparation of a compound of the formula I or a salt thereof

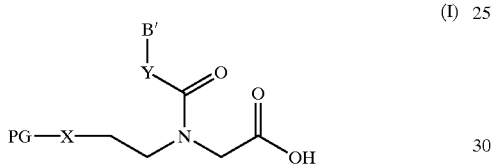
(I)

wherein

PG is a trityl type protective group which is labile to weak acids, and is selected from triphenylmethyl (Trt), (4-methoxyphenyl)-diphenylmethyl (Mmt), (4-methylphenyl)-diphenylmethyl (Mtt), di-(4-methoxyphenyl)phenylmethyl (Dmt), and 9-(9-phenyl)-xanthenyl (pixyl);

X is NH, O, or S;

Y is CH$_2$; and

B' is a base selected from adenine, cytosine, guanine, thymine, uracil, purine, 2,6-di-aminopurine, 7-deazaadenine, 7-deazaguanine, $N^4N^4$-ethanocytosine, $N^6N^6$-ethano-2,6-diaminopurine, 5-methylcytosine, 5-($C_2$–$C_6$)alkynyluracil, 5-($C_2$–$C_6$)alkynylcytosine, 5-fluorouracil, and pseudoisocytosine, wherein any exocyclic amino or hydroxyl group is protected by a protective group, or B' is further selected from imidazole, triazole, and nitroimidazole;

said process comprising reacting a compound of the formula (II)

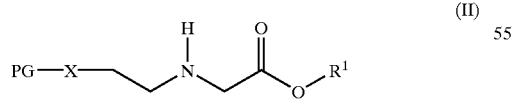
(II)

wherein PG and X are as defined above, and R¹ is hydrogen or a tri-substituted silyl protective group, with a compound of the formula (V)

B'—CH$_2$—CO—R²      (V), wherein B' is as defined above, and R² is a halogen or a radical of an active ester, at 0–40° C. in a suitable solvent or mixtures of these solvents, and wherein, when R¹ is a tri-substituted silyl protective group, it is removed after reaction with a compound of formula (V) by adding water or alcohol to the reaction mixture, and wherein the resulting compound of the formula I may, optionally, be converted to a salt.

3. A process for the preparation of a compound of the formula I or a salt thereof

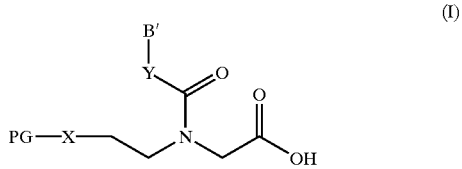
(I)

wherein

PG is a trityl type protective group which is labile to weak acids, and is selected from triphenylmethyl (Trt), (4-methoxyphenyl)-diphenylmethyl (Mmt), (4-methylphenyl)-diphenylmethyl (Mtt), di-(4-methoxyphenyl)phenylmethyl (Dmt), and 9-(9-phenyl)-xanthenyl (pixyl);

X is NH, O, or S;

Y is CH$_2$; and

B' is a base selected from adenine, cytosine, guanine, thymine, uracil, purine, 2,6-di-aminopurine, 7-deazaadenine, 7-deazaguanine, $N^4N^4$-ethanocytosine, $N^6N^6$-ethano-2,6-diaminopurine, 5-methylcytosine, 5-($C_2$–$C_6$)alkynyluracil, 5-($C_2$–$C_6$) alkynylcytosine, 5-fluorouracil, and pseudoisocytosine, wherein any exocyclic amino or hydroxyl group is protected by a protective group, or B' is further selected from imidazole, triazole, and nitroimidazole;

said process comprising reacting a compound of the formula (II)

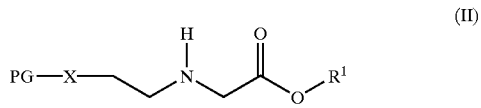
(II)

wherein PG and X are as defined above, and R¹ is an ester protective group, with a monohaloacetic acid halide in a suitable solvent with an auxiliary base to give the compound of the formula (VI)

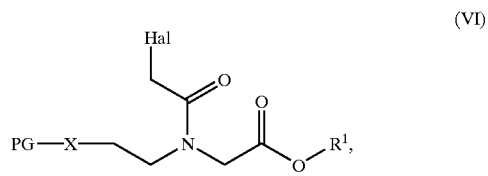
(VI)

wherein Hal is Cl, Br or I, and PG, X, and R¹ are as defined above, reacting this intermediate of the formula (VI) with the optionally protected B'H and an auxiliary base in a suitable solvent to give the compound of the formula (IV)

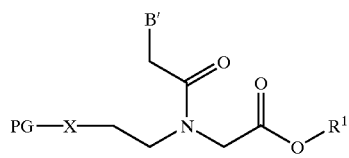 (IV)

wherein PG, X, B', and R¹ are as defined above, and subsequently converting this compound to a compound of the formula (I) by eliminating the ester protective group R¹ using an alkali metal hydroxide solution or enzymatically with the aid of esterases or lipases at 0–50° C. in a suitable solvent or mixtures of these solvents, and wherein the resulting compound of the formula I may, optionally, be converted to a salt.

4. A process for the preparation of a compound of the formula I or a salt thereof

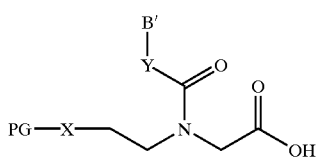 (I)

wherein
PG is a trityl type protective group which is labile to weak acids, and is selected from triphenylmethyl (Trt), (4-methoxyphenyl)-diphenylmethyl (Mmt), (4-methylphenyl)-diphenylmethyl (Mtt), di-(4-methoxyphenyl)phenylmethyl (Dmt), and 9-(9-phenyl)-xanthenyl (pixyl);
x is NH, O, or S;
Y is O or NH; and
B' is a base selected from adenine, cytosine, guanine, thymine, uracil, purine, 2,6-di-aminopurine, 7-deazaadenine, 7-deazaguanine, $N^4N^4$-ethanocytosine, $N^6N^6$-ethano-2,6-diaminopurine, 5-methylcytosine, 5-($C_2$–$C_6$)alkynyluracil, 5-($C_2$–$C_6$)alkynylcytosine, 5-fluorouracil, and pseudoisocytosine, wherein any exocyclic amino or hydroxyl group is protected by a protective group, or B' is further selected from imidazole, triazole, and nitroimidazole;

said process comprising reacting a compound of the formula (II)

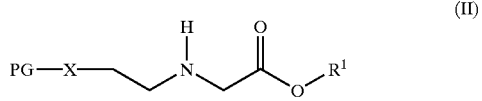 (II)

wherein PG and X are as defined above, and R¹ is a ester protective group, with a compound of the formula (VII)

 (VII), wherein B' and Y are as defined above, and R³ is Cl, 4-nitrophenoxy, or N-succinimido-oxy, at 0–40° C. in a suitable solvent or mixtures of these solvents, and subsequently eliminating the ester protective group R¹ using an alkali metal hydroxide solution or enzymatically with the aid of esterases or lipases at 0–50° C. in a suitable solvent or mixtures of these solvents, and wherein the resulting compound of the formula I may, optionally, be converted to a salt.

5. The process of claim 2, wherein
PG is Mmt or Dmt;
R¹ is hydrogen or trimethylsilyl; and
R² is chloride, an ester radical selected from a radical of 1-hydroxybenzo-triazole (Obt), a radical of 4-oxo-3,4-dihydro-1,2,3-benzotriazin-3-yloxy (OObt), a radical of pentafluorophenol (OPfp), a radical of N-hydroxysuccinimide (ONSu), or a radical of 4-nitrophenol (ONp).

6. The process of claim 3, wherein
PG is Mmt or Dmt;
R¹ is methyl or ethyl; and
Hal is Chlorine or Bromine.

7. The method of claim 4, wherein
PG is Mmt or Dmt;
R¹ is methyl or ethyl; and
R² is a radical of N-hydroxysuccinimide (ONSU) or a radical of 4-nitrophenol (ONp).

* * * * *

UNITED STATES PATENT AND TRADEMARK OFFICE
CERTIFICATE OF CORRECTION

PATENT NO.   : 6,465,650 B1
DATED         : October 15, 2002
INVENTOR(S)  : Gerhard Breipohl et al.

It is certified that error appears in the above-identified patent and that said Letters Patent is hereby corrected as shown below:

<u>Title page,</u>
Item [57], ABSTRACT,
Line 1, "provides a processes" should read -- provides processes --.
Line 10, "(III)" adjacent the structural formula, should read -- (III), --.
Line 15, "B'–$CH_2$–CO–$R^3$" should read -- B'–Y–CO–$R^3$ --.

<u>Column 30,</u>
Line 31, "(4-methoxyphenyl)diphenylmethyl" should read -- (4-methoxyphenyl)-diphenylmethyl --.
Line 34, "xanthenyl(pixyl)" should read -- xanthenyl (pixyl) --.
Line 43, after "amino" delete the line break.

<u>Column 33,</u>
Line 35, "x is" should read -- X is --.

<u>Column 34,</u>
Line 42, "(ONSU)" should read -- (ONSu) --.

Signed and Sealed this

Sixth Day of May, 2003

JAMES E. ROGAN
*Director of the United States Patent and Trademark Office*